(12) United States Patent
Bergmann-Leitner et al.

(10) Patent No.: US 8,470,560 B2
(45) Date of Patent: Jun. 25, 2013

(54) CR-2 BINDING PEPTIDE P28 AS MOLECULAR ADJUVANT FOR DNA VACCINES

(75) Inventors: Elke S. Bergmann-Leitner, Kensington, MD (US); Evelina Angov, Bethesda, MD (US); George C. Tsokos, Boston, MA (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 157 days.

(21) Appl. No.: 12/680,758

(22) PCT Filed: Oct. 3, 2008

(86) PCT No.: PCT/US2008/078864
§ 371 (c)(1),
(2), (4) Date: Mar. 30, 2010

(87) PCT Pub. No.: WO2009/046388
PCT Pub. Date: Apr. 9, 2009

(65) Prior Publication Data
US 2010/0255075 A1  Oct. 7, 2010

Related U.S. Application Data

(60) Provisional application No. 60/998,460, filed on Oct. 3, 2007.

(51) Int. Cl.
*C12P 21/06* (2006.01)
*A61K 39/015* (2006.01)

(52) U.S. Cl.
USPC ... 435/69.7; 435/69.1; 424/191.1; 424/272.1; 424/450

(58) Field of Classification Search
None
See application file for complete search history.

(56) References Cited

U.S. PATENT DOCUMENTS

| 6,919,319 B2 | 7/2005 | Garzino-Demo et al. |
| 2004/0191252 A1 | 9/2004 | Taylor et al. |
| 2005/0265974 A1 | 12/2005 | Pau et al. |

FOREIGN PATENT DOCUMENTS

| EP | 0120694 A2 | 3/1984 |
| EP | 0125023 A1 | 11/1984 |
| EP | 184187 A2 | 6/1986 |
| EP | 239400 A2 | 9/1987 |
| GB | 1288638 A | 10/1987 |
| WO | WO92/01047 A1 | 1/1992 |
| WO | WO93/06213 A1 | 4/1993 |
| WO | WO93/11161 A1 | 6/1993 |
| WO | WO94/13804 A1 | 6/1994 |

OTHER PUBLICATIONS

Crystal RG. Science 270:404-410.1995).*
Verma and Somia (Verma IM and Somia N. Nature 389: 239-242. 1997.*
Kmiec EB. American Scientist 87:240-247, 1999.*
Romano et al. Stem Cells 2000; 18:19-39.*
Anderson WF. Nature 392 (SUPP):25-30, 1998.*
Bergmann-Leitner, Elke S. et al., C3d-defined complement receptor-binding peptide p28 conjugated to circumsporozoite protein provides protection against *P. berghei*, Vaccine, Sep. 4, 2007, pp. 7732-7736, vol. 25, Elsevier Ltd.

* cited by examiner

*Primary Examiner* — Padma V Baskar
(74) *Attorney, Agent, or Firm* — Elizabeth Arwine

(57) ABSTRACT

The invention is an DNA vaccine and method of use thereof for modulating the immune response against the circumsporozoite protein (CSP) of malaria parasites, using the CR2 binding motifs of C3d, especially p28.

10 Claims, 6 Drawing Sheets

| | |
|---|---|
| STOP, SENSE<br>SEQ. ID. NO. 9 | 5´-CTAGCGGATCCTGAA-3´ |
| STOP, NONSENSE<br>SEQ. ID. NO. 10 | 5´-GATCTTCAGGATCCG-3´ |
| ADAPTER, SENSE<br>SEQ. ID. NO. 11 | 5´-TTAGGATCCGAGGAATTCTGA-3´ |
| ADAPTER, NONSENSE<br>SEQ. ID. NO. 12 | 5´-GATCTCAGAATTCCTCGGATCCTAAAT-3´ |
| PCR, SENSE<br>SEQ. ID. NO. 13 | 5´-GCTAGCACATGTGGTTCTGG-3´ |
| PCR, NONSENSE<br>SEQ. ID. NO. 14 | 5´-TTTACCTATTTACAAGTTCACCTTAAGGAGTCTAGAAT-3´ |

FIG. 2

| VACCINE[a] | VACCINE EFFICACY[b] | | | |
|---|---|---|---|---|
| | 1. CHALLENGE | | 2. CHALLENGE | |
| | n INFECTED ANIMALS/ n VACCINATED | EFFICACY COMPARED TO pcDNA | n INFECTED ANIMALS/ n VACCINATED | EFFICACY COMPARED TO pcDNA |
| pcDNA | 9/10 | | 10/10 | |
| CSP(-A) | 0/10 | 100 (p = 0.002) | 4/10 | 60% (p = 0.04) |
| CSP-3p28 | 0/10 | 100 (p = 0.002) | 0/10 | 100% (p = 0.002)[c] |

[a]Mice were immunized three times and challenged 2 weeks after the last immunization. Mice were challenged by subcutaneous injection of 4000 live P. berghei sporozoites.
[b]Data are expressed as % efficacy = 1-(Iv/Ic), where Iv and Ic represent the incidence rates (% infected animals in each group) in the vaccinated and control plasmid group, respectively. The significance of the differences between the proportions of infected animals in the vaccine and pcDNA control groups was determined by using $\chi^2$ (two tails).
[c]p=0.043 when comparing vaccine efficacy of CSP(-A) with CSP-3p28 vaccine (Fisher's exact test)

FIG. 5

CR-2 BINDING PEPTIDE P28 AS MOLECULAR ADJUVANT FOR DNA VACCINES

CROSS-REFERENCE TO RELATED APPLICATIONS

This application claims priority to U.S. Provisional Application 60/998,460, filed on Oct. 3, 2007, the entirety of which being incorporated herein by this reference.

FIELD AND BACKGROUND OF THE INVENTION

The invention relates to the field of medicine and biotechnology. More particularly, the invention relates to the use of a recombinant model antigen DNA vaccine incorporating tandem copies (as, for example linear concatamers) of the synthetic peptides derived from the CR2 binding motif of the C3d domain of the third component (C3) of the human complement system. Furthermore, this inventions relates to a method and kit for the implementation of said method of such a construct as a vaccine against malaria infections and as a treatment of the same.

Background on the Malarial Disease

Malaria currently represents one of the most prevalent infections in tropical and subtropical areas throughout the world. Per year, malaria infections lead to severe illnesses in hundreds of million individuals worldwide, while it kills 1 to 3 million people, primarily in developing and emerging countries every year. The widespread occurrence and elevated incidence of malaria are a consequence of the increasing numbers of drug-resistant parasites and insecticide-resistant parasite vectors. Other factors include environmental and climatic changes, civil disturbances, and increased mobility of populations.

Malaria is caused by the mosquito-borne hematoprotozoan parasites belonging to the genus *Plasmodium*. Four species of *Plasmodium* protozoa (*P. falciparum, P. vivax, P. ovale* and *P. malariae*) are responsible for the disease in humans; many others cause disease in animals, such as *P. yoelii* and *P. berghei* in mice. *P. falciparum* accounts for the majority of infections and is the most lethal type ("tropical malaria"). Malaria parasites have a life cycle consisting of several stages. Each stage is able to induce specific immune responses directed against the corresponding occurring stage-specific antigens.

Malaria parasites are transmitted to man by several species of female *Anopheles* mosquitoes. Infected mosquitoes inject the "sporozoite" form of the malaria parasite into the mammalian bloodstream. Sporozoites remain for a few minutes in the circulation before invading hepatocytes. At this stage, the parasite is located in the extra-cellular environment and is exposed to antibody attack, mainly directed to the "circumsporozoite" (CS) protein (CSP), a major component of the sporozoite surface. Once in the liver, the parasites replicate and develop into so-called "schizonts." These schizonts occur in a ratio of up to 20,000 per infected cell. During this intracellular stage of the parasite, main players of the host immune response are T-lymphocytes, especially CD8+ T-lymphocytes (Bruna-Romero O., 2001A). After about one week of liver infection, thousands of so-called "merozoites" are released into the bloodstream and enter red blood cells, becoming targets of antibody-mediated immune response and T-cell secreted cytokines. After invading erythrocytes, the merozoites undergo several stages of replication and transform into so-called "trophozoites" and into schizonts and merozoites, which can infect new red blood cells. This stage is associated with overt clinical disease. A limited amount of trophozoites may evolve into "gametocytes," which is the parasite's sexual stage. When susceptible mosquitoes ingest erythrocytes, gametocytes are released from the erythrocytes, resulting in several male gametocytes and one female gametocyte. The fertilization of these gametes leads to zygote formation and subsequent transformation into ookinetes, then into oocysts, and finally into salivary gland sporozoites.

Malaria Vaccines Incorporating CSP Antigens

Current strategies for developing effective malaria vaccines are to elicit 1) humoral responses against sporozoite surface antigen (Ag) to reduce infection of the liver, 2) cellular responses against hepatic stages to kill infected liver cells and reduce the subsequent blood stage infection, 3) humoral responses against erythrocytic stage Ag to eliminate residual infection and disease, and 4) humoral responses against sexual stage Ag to reduce transmission. (Wolfgang W. Leitner *. M., 1997). One candidate for inclusion is the circumsporozoite protein (CSP) which is present in three developmental stages, including sporozoites and infected hepatocytes (Nussenzweig. V., 1989) and exoerythrocytic merozoites, but not erythrocytic merozoites (Atkinson, 1989).

The CS protein is the only *P. falciparum* antigen demonstrated to consistently prevent malaria when used as the basis of active immunization in humans against mosquito-borne infection, albeit at levels that are often insufficient. Theoretical analysis has indicated that the vaccine coverage, as well as the vaccine efficiency, should be above 85% or, otherwise, mutants that are more virulent may escape (Clyde D. F., 1973).

The sporozoite stage of malaria parasites carries CSP on its outer surface (Aikawa, 1981) which expresses a unique immunodominant epitope recognized by immunized or repeatedly infected hosts (Zavala F. A., 1983). Sera from mice immunized with *Plasmodium berghei* sporozoites immunoprecipitate a single 44,000Mr protein, the circumsporozoite (CS) protein (CSP), from extracts of surface-labeled sporozoites (Zavala F. A., 1983). Immunoprecipitation of extracts of metabolically labeled sporozoites with a monoclonal antibody (3D11) directed to the CSP demonstrated that the 44,000Mr membrane form is derived from a 54,000-Mr intracellular precursor (Zavala F. A., 1983). The CSP from monkey and human malaria parasites contains amino and carboxy-terminal regions of relatively low immunogenicity which flank a central region of highly immunogenic, tandemly repeated amino acid units, the sequences of which differ from species to species (Damem, 1984). Monoclonal antibodies to the repeated amino acid units neutralize parasite infectivity (Nussenzweig, 1969), suggesting that CSP might be useful as sporozoite-stage vaccines.

The central region of the CSP contains tandem repetitive peptide sequences that appear to be the dominant targets for Ab responses during infection (Nussenzweig. V., 1989). The N and C-terminal regions flanking the central CSP repeats contain several immunologically and structurally important features, such as MHC class I and II epitopes (Romero, 1990), and peptide structures that appear to be important for sporozoite invasion of hepatocytes (Aley, 1986). CSP-specific immune responses have been induced with various synthetic peptides and fragments or full-length recombinant proteins (Egan, 1987). The responses were B cell (Egan, 1987) or T cell dependent and in the case of T cell responses, were either CD4 or CD8 dependent (Migliorini, 1993). However, only a few of the immunogens induced responses that reduced the infection rate upon challenge (Egan, 1987). While some CSP repeat region-specific mAbs reduce infection rates (Potocnjak, 1980), repeat region-specific polyclonal immune sera have little protective efficacy (Egan, 1987). Immune responses to a sulfatide binding motif from *P. falciparum* CSP can reduce *P. berghei* infection rates in vaccinated mice (Chatterjee. S., 1995). CSP-specific CD8+ T cell clones prepared by vaccination with a synthetic peptide reduced infection rates in recipient mice after adoptive transfer, but active immunization with the same peptide did not affect infection rates (Nussenzweig. V., 1989). Vaccination of BALB/c mice with recombinant vaccinia expressing *P. berghei* CSP induced CTL and reduced the infection rate upon challenge. Thus, as a sporozoite surface Ag, a hepatic stage Ag, and an exoerythrocytic merozoite surface Ag, CSP is a good target for neutralizing Ab as well as cellular immune responses (Wolfgang W. Leitner *. M., 1997).

The C terminus of the circumsporozoite protein (CSP) is anchored to the parasite cell membrane by a glycosylphosphatidylinositol (GPI) glycolipid. This GPI signal sequence functions poorly in heterologous eukaryotic cells, causing CSP retention within internal cell organelles during genetic immunization. Cellular location of antigen has quantitative and qualitative effects on immune responses induced by genetic immunization. Removal of the GPI signal sequence has a profound effect on induction and efficacy of CSP-specific immune response after genetic immunization of BALB/c mice with a gene gun (Sandra Scheiblhofer, 2001). The CSP produced from a plasmid lacking the GPI anchor signal sequence (CSP−A) is secreted and soluble, but that produced by a CSP+A plasmid is not. The CSP−A plasmid induces a highly polarized Th2 type response, in which the CSP-specific IgG antibody titer is three- to fourfold higher, and the protective effect is significantly greater than that induced by a CSP+A plasmid. Thus, engineering plasmid constructs for proper cellular localization of gene products is a primary consideration for the preparation of optimally efficacious DNA vaccines. (Sandra Scheiblhofer, 2001).

During genetic immunization with plasmid DNA, the amount of plasmid-associated CpG motif administered has the strongest effect on the quantitative and qualitative aspects of immune responses (Klinman, 1997). Another important factor is the physical form of the expressed protein (Barry, 1997). Immunization of mice with plasmids expressing secreted soluble antigen induces strong humoral responses of the Th2 type, as measured by induction of IgG1 isotype antibodies, whereas immunization with plasmid expressing cytoplasmic and membrane-anchored antigens tends to induce a more balanced response as measured by induction of IgG2a isotype antibodies (Forms, 1999).

DNA Vaccinations—a Background

DNA vaccination has become the fastest growing field in vaccine technology following reports at the beginning of the 90's that plasmid DNA induces an immune response to the plasmid-encoded antigen (Wolff J A, 1990). However, DNA vaccination in many cases is hampered by poor efficacy. Thus, as discussed below, various strategies must be developed to improve immune responses induced by genetic vaccines.

In contrast to vaccines that employ recombinant bacteria or viruses, genetic vaccines consist only of DNA (as plasmids) or RNA (as mRNA), which is taken up by cells and translated into protein. In case of gene-gun delivery, plasmid DNA is precipitated on to an inert particle (generally gold beads) and forced into the cells with a helium blast. Transfected cells then express the antigen encoded on the plasmid resulting in an immune response. Like live or attenuated viruses, DNA vaccines effectively engage both MHC-I and MHC-II pathways allowing for the induction of CD8+ and CD4+ T cells whereas antigen present in soluble form, such as recombinant protein, generally induces only antibody responses (Wolfgang W. Leitner H. Y., 1999).

Because genetic vaccines are relatively inexpensive and easy to manufacture and use, their immunogenicity and efficacy have been analyzed in a large number of systems and results from preclinical studies have supported human clinical trials. Studies have rapidly moved from small laboratory animals to primates and clinical trials are currently being conducted for diseases such as cancer, HIV-infection, or malaria (Hoffman S L, 1997).

The quick acceptance of genetic vaccines in experimental settings is due to the many advantages this strategy has over traditional vaccines. However, the efficacy of genetic vaccines in many systems has not proven to be satisfactory, leading some to conclude that genetic vaccines are not a viable alternative to conventional vaccines and will never replace them (Manickan E, 1997). Some studies, however, purport that DNA vaccines are more efficacious than some established vaccines based on recombinant proteins, recombinant viruses, or both (Schirmbeck R, 1996). Indeed, DNA vaccines can circumvent many of the problems associated with recombinant protein-based vaccines, such as high costs of production, difficulties in purification, incorrect folding of antigen and poor induction of CD8+ T cells. DNA also has clear advantages over recombinant viruses, which are plagued with the problems of pre-existing immunity, risk of insertion-muta-genesis, loss of attenuation or spread of inadvertent infection (Restifo N, 1999).

DNA vaccines usually consist of plasmid vectors (derived from bacteria) that contain heterologous genes (transgenes) inserted under the control of a eukaryotic promoter, allowing protein expression in mammalian cells (HL, 1997). An important consideration when optimising the efficacy of DNA vaccines is the appropriate choice of plasmid vector. The basic requirements for the backbone of a plasmid DNA vector are a eukaryotic promoter, a cloning site, a polyadenylation sequence, a selectable marker and a bacterial origin of replication (Gurunathan S, 2000). A strong promoter may be required for optimal expression in mammalian cells. For this, some promoters derived from viruses such as cytomegalovirus (CMV) or simian virus 40 (SV40) have been used. A cloning site downstream of the promoter should be provided for insertion of heterologous genes, and inclusion of a polyadenylation (polyA) sequence such as the bovine growth hormone (BGH) or SV40 polyadenylation sequence provides stabilisation of mRNA transcripts. The most commonly used selectable markers are bacterial antibiotic resistance genes, such as the ampicillin resistance gene. However, since the ampicillin resistance gene is precluded for use in humans, a kanamycin resistance gene is often used. Finally, the *Escherichia coli* ColE1 origin of replication, which is found in plasmids such as those in the pUC series, is most often used in DNA vaccines because it provides high plasmid copy numbers in bacteria enabling high yields of plasmid DNA on purification (Helen S Garmory, 2003).

Genetic vaccines can be delivered into the host by several routes and methods. Needle-injection into muscle tissue and into the skin is the most commonly used method (Wolff J A, 1990). Also the spleen and a variety of mucosal surfaces (Wang B, 1997) including those of the nose and gut have been targeted (Wolfgang W. Leitner H. Y., 1999). Scale-up from small rodents to larger animals and humans may not be an obstacle: A given DNA-dose may effectively induce an immune response regardless of body size (Cox G J, 1993). Despite the large number of genetic vaccine-studies conducted so far, many of the results are difficult to compare and inconsistent. A number of factors determine the magnitude and type of immune response induced by plasmid DNA (see Table in FIG. 1).

Genetic vaccines may mimic some aspects of the natural infection of host-cells. However, microorganisms contain surface-molecules such as LPS and a variety of soluble factors that function as adjuvants, alerting the immune system to 'danger' by inducing inflammation. The potency of genetic vaccines may be significantly enhanced by mimicking these signals with synthetic adjuvants such as QS21 or monophosphoryl lipid A (MPL) (Sasaki S, 1997). However, DNA plasmids without adjuvant are able to induce remarkably strong immune responses to the encoded antigen.

Because myocytes are able to take up some of the plasmid injected into the muscle the mechanism of intramuscular immunization seemed very straightforward (see FIG. 2) (Wolfgang W. Leitner H. Y., 1999). However, muscle is not considered an immunologically relevant tissue as myocytes lack the characteristics of antigen-presenting cells (APC) such as MHC-II expression, costimulatory molecules or marked cytokine-secretion. Even the co-expression of costimulatory molecules or cytokines like GM-CSF or IL-12 is insufficient to turn non-hematopoetic cells into efficient APC (Iwasaki A, 1997). Thus, it seems unlikely that muscle tissue is the immune activating component.

Two possible scenarios could explain the mechanism of immune-priming by intramuscularly injected genetic vaccines (see FIG. 2). First, myocytes are the antigen-factories that supply professional APCs with antigen for the induction of an immune response in the form of full-length protein or peptides (Spier, 1996). Alternatively, resident APCs may be transfected directly and the antigen that is expressed by transfected myocytes is an irrelevant side-product. In either case, the antigen-expressing bone marrow-derived APCs then migrate to lymph nodes where they activate the T and B lymphocytes. Transfected myocytes may also serve as plasmid-depots for continued APC-transfection. Because myocytes expressing the antigen are subject to CTL-lysis (Davis H L, 1997), plasmid released from these myocytes may be picked up by monocytes migrating through the muscle (Wolfgang W. Leitner H. Y., 1999).

Both bone marrow-derived APC (BM-APC) and plasmid-carrying macrophages from the injected muscle to lymph nodes has been observed (Wolfgang W. Leitner H. Y., 1999). The crucial role of DC is also supported by the observation that subcutaneous DNA-injection is very inefficient since this tissue lacks Langerhans cells (Condon C, 1998).

In contrast to muscle, skin has important immunological functions as it represents the 'first line of defence' of the immune system. Throughout the epidermis, specialized DC form a 3-dimensional network to assure tight immune-surveillance of the skin. Infections agents stimulate DC to pick up antigen and after migrating to the local lymph nodes initiate an immune response (MC, 1997). The main methods of plasmid-DNA delivery to the skin, by needle injection or by gene-gun, differ in several respects. While needle injection requires relatively large amounts of plasmid (similar to the 50-100 μg dose used in intramuscular immunization), the amount of plasmid required for gene-gun immunization has been titrated down to a few nanogram (Degano P, 1998). As in myocyte-transfection after intramuscular immunization, plasmid can be actively taken up by skin cells but only few cells are transfected after intradermal injection (Wolfgang W. Leitner H. Y., 1999).

When delivered by gene-gun, the plasmid solubilizes when the plasmid-coated gold bullet penetrates the cells in the skin. Thus, plasmid is directly deposited into cells transfecting up to 20% of the cells in the target-area (Williams R S, 1991). Tissue stress resulting from the blast may contribute to the activation of DC. Indeed, the total number of DC in the skin-draining lymphoid tissue increases enormously after gene-gun immunization, although the majority of these cells do not carry the plasmid. The small amounts of immunostimulatory DNA delivered with the gene gun may not be sufficient to mediate a Th1-type response allowing Th2-type responses to emerge (Barry M A, 1997). By modifying the immunization-regimen, either IgG1 or mixed IgG1/IgG2-responses can be induced by gene-gun immunization (Leitner W W, 1997). Furthermore, a gene gun-induced Th2-type response can be switched to a Th1-type response by co-delivering the genes for IL-2, -7 or -12 (Prayaga S K, 1997) (see FIG. 3).

Improving the Efficacy of DNA Vaccines

A large number of approaches have been used in an attempt to improve the often poor efficacy of DNA vaccines. Because the efficacy of DNA vaccines in many systems has not been satisfactory, the most simple and unexpectedly effective strategy is increasing the intervals between immunizations and, thereby, the 'rest-period' of the immune system. In addition, many elements of the plasmid can be optimized for use of the vector as a DNA vaccine (Wolfgang W. Leitner H. Y., 1999). Based on the idea that more antigen is better, most DNA vaccines use strong viral promoters and are geared towards maximum expression. Other sequences that can be optimized in a plasmid include introns, enhancers and poly-adenylation signals, see, e.g. (Bohm W, 1996), (Danko I, 1997) and (Montgomery D L, 1993). Without a doubt, one of the outstanding features of DNA immunization is the opportunity to co-deliver information together with to the antigen-coding sequence on the plasmid DNA. In recent years several strategies have successfully been used to modulate the immune response after DNA immunization, such as: (i) different modes and sites of gene delivery, (ii) co-delivery of genes or adjuvant molecules with regulatory and/or stimulatory properties and (iii) modification of the vector sequences by inserting or deleting cytosolic or endosomal transport signals.

To improve the immunogenicity of an antigen encoded by a genetic vaccine, functional sequences like the intracellular domain or the trans-membrane sequence can be eliminated (Chen Y, 1998). Antigens can be targeted to the Class-I or Class-II processing pathways with the addition of sequences designed to direct intracellular trafficking. Finally, immunodominant epitopes from antigens can be expressed as minigenes, or they can be buried within unrelated, but highly immunogenic core-sequences (Ciernik I F, 1996). This may be especially useful in cases where 'full-length' proteins are not suitable as vaccine candidates, because they are toxic for the host or immunosuppressive. Antigenic proteins can be maximally truncated, leaving only defined epitopes for B or T cells. Antigens consisting of CD8+ T cell-epitopes alone are sufficient to induce CTLs as this approach has also successfully been used for CD4+-T cell epitopes (Casares S, 1997). To overcome MHC-restriction of individual epitopes or to induce a broader range of effector-cells, it is possible to deliver multiple contiguous minimal epitopes in form of a 'polytope'. To improve MHC-1-loading, endoplasmic reticulum (ER) insertion signal sequences can be attached to minigenes. These sequences can facilitate the targeting of the antigen to the ER, where MHC-I molecules are complexed with antigen. This approach was pioneered in the vaccinia system and also works for peptide-immunization (Minev B R, 1994). An adenovirus leader-sequences has successfully been used to target DNA vaccine encoded CD8+ T cell epitopes to the ER (Ciernik I F, 1996).

Helper epitopes, such as the hepatitis B core-antigen, can activate B cells and elicit strong T cells responses adding significantly to DNA-based vaccines against hepatitis (Kuhrober A, 1997).

Cytokines, such as IL-2, IL-6, IL-7 and especially IL-12 can significantly improve vaccine-induced immune responses, accelerating and augmenting it as well as directing it, for example, towards a Th1- or Th2-type response (Irvine K R, 1996). Other useful cytokine adjuvants include GM-CSF, a cytokine thought to recruit and mature dendritic cells (Mellstedt H, 1999). Besides using exogenous factors, cytokines as well as chemokines encoded on plasmid DNA or as cDNA have been used to study, modulate or enhance a DNA vaccine induced immune response. One study shows the conversion of a non-immunogenic antigen into a DNA vaccine by fusing it to the genes for chemokines (Biragyn A, 1999).

To develop a T cell response, APCs have to deliver two signals to the T cell: one signal is from the MHC/peptide complex to the T cell receptor, the second is from a costimulatory molecule, of which B7 is perhaps the most important and best characterized. In the absence of costimulation, T cells may become anergic preventing self-reactive cells from producing auto-reactivity. B7.1 and B7.2 are expressed on professional APC and on a variety of other tissues after exposure to inflammatory cytokines (Pechhold K, 1997).

Co-delivery of B7.1 with a malaria antigen (Pb-CSP) by gene gun significantly increased the protective effect of a low-expressing plasmid, but not of a high expresser plasmid (Wolfgang W. Leitner H. Y., 1999)

Non-methylated, palindromic DNA-sequences containing CpG-oligodinucleotides (CpG-ODN) can activate an 'innate' immune response by activating monocytes, NK cells, dendritic cells and B-cells in an antigen-independent manner (immunostimulatory DNA sequences, ISS) (Wolfgang W. Leitner H. Y., 1999). CpG-ODN have been reported by one group to be as effective an adjuvant as Complete Freund's Adjuvant and to be without significant toxicity (Weiner G J, 1997). In addition, CpG motifs enhance the expression of various co-stimulatory ligands such as CD80, CD40, and ICAM-1 on APCs. In the case of DNA vaccines they can either be co-administered with plasmid-DNA in the form of oligonucleotides or the number of ISS on the plasmid-backbone can be increased.

The delivery of the same antigen multiple times using carriers with little or no immunogenic crossreactivity (heterologous prime-boost-regimen) provides several advantages over the repeated delivery of an antigen with the same carrier (homologous boosting). The repeated use of any given recombinant virus-based vaccine may be impaired by anamnestic responses to the carrier itself (Restifo N, 1999). Including DNA in these regimens may also shift the response towards Th1, even when a Th2-type response was initiated with recombinant protein (Li X, 1998). Heterologous boosting yielded full protection in the *P. berghei* malaria model when plasmid immunization was followed by administration of recombinant vaccinia virus. Homologous boosting was weak or ineffective in this model (Sedegah M, 1998).

'Self-replicating' genetic vaccines are designed to overcome the poor efficacy of some current DNA-based and RNA-based genetic vaccines. The idea and the elements for this new generation of vaccines come from members of the Alphavirus genus, which includes Sindbis virus, Semliki Forest virus (SFV) and Venezuelan equine encephalitis (VEE) virus. These RNA viruses contain a single copy of positive-stranded RNA encapsidated by a protein/lipid envelope. The viral RNA encodes its own RNA replicase, an autoproteolytic polyprotein that cleaves itself into four non-structural protein components (nsP1-4) (Berglund P, 1996). Upon infecting a cell, the viral RNA first translates the replicase complex, which in turn drives its own RNA replication. The replicase complex then synthesizes a genomic negative-strand (antisense RNA), which is used as a template for the synthesis of the genomic positive-stand RNA as well as a subgenomic RNA encoding the structural viral proteins (see FIG. 4). The genes for structural proteins can be replaced with the gene for the antigen of interest to construct powerful replicase-based vaccines (Caley I J, 1997).

Theoretically up to 200,000 copies of RNA can be produced in a single cell within 4 h and expression of the encoded antigen can be as much as 25% of total cell protein (Rolls M M, 1994). The alphavirus replicase functions in a broad range of host cells (mammalian, avian, reptilian, amphibian and insect cells) (Rolls M M, 1994). Replication takes place in the cytoplasm of the host cell and, therefore, is independent of the host's replication system. All the above features, i.e. high level expression, broad host range and cytoplasmic replication, are useful features in genetic vaccine development.

To facilitate vaccine production, genomic alphavirus RNA alone can be used as a vaccine vehicle. The in vitro transcribed self-replicating RNA contains sequences coding for the SFV replicase and a model antigen. DNA-based vaccines can also be constructed by inserting a strong promoter like the human CMV immediate promoter/enhancer element to initiate the transcription of the full length 'genomic' RNA in the nucleus (Tubulekas I, 1997). Replicase-based DNA vaccines may be significantly more immunogenic and efficacious than conventional DNA-plasmid vaccines when low doses of the vaccine are given. Indeed, nanogram amounts of replicase-based vaccine can induce antigen-specific antibody and CD8+ T cell responses (Wolfgang W. Leitner H. Y., 1999).

Furthermore, it has been demonstrated that inclusion of the CMV intron A improved the level of expression of transgenes expressed by the CMV promoter or other promoter/enhancers (Chapman B S, 1991). However, some widely used virally-derived promoters, such as the CMV promoter, may not be suitable for some gene therapy applications since treatment with interferon-γ or tumour necrosis factor-α may inhibit transgene expression from DNA vaccines containing these promoters (Harms J S, 1999). Thus, alternatives to the CMV promoter have been sought. For example, the desmin promoter/enhancer, which controls expression of the muscle-specific cytoskeletal protein desmin, was used effectively to drive expression of the hepatitis B surface antigen priming both humoral and cellular immunity against the antigen. These responses were shown to be of a comparable magnitude to those in mice immunised with comparable DNA vaccines containing the CMV promoter. Other tissue-specific promoters that have been studied include the creatine kinase promoter, also specific to muscle cells and the metallothionein and 1,24-vitaminD(3)(OH)(2) dehydroxylase promoters, both of which are specific to keratinocytes (Itai K, 2001).

Since the rate of transcriptional initiation is generally increased by the use of strong promoter/enhancers, the rate of transcriptional termination may become rate-limiting (NJ, 1989). In addition, the efficiency of primary RNA transcript processing and polyadenylation is known to vary between the polyadenylation sequences of different genes. Thus, the polyadenylation sequence used within a DNA vaccine may also have significant effects on transgene expression. For example, it was demonstrated that the commonly used SV40 polyadenylation sequence was less efficient than the minimal rabbit β-globin and bovine growth hormone polyadenylation sequences in mouse liver, although addition of a second SV40 enhancer downstream of the SV40 polyadenylation signal did increase expression to a level comparable to the other signals (Xu Z-L, 2001). Therefore, it is possible that the strategy of inserting a second SV40 enhancer downstream of a SV40 polyadenylation sequence may be utilised in the construction of more efficient vectors.

Sequences flanking the AUG initiator codon within mRNA influence its recognition by eukaryotic ribosomes. As a result of studying the conditions required for optimal translational efficiency of expressed mammalian genes, the 'Kozak' consensus sequence has been shown to be important (M, 1997). It has been proposed that this defined translational initiating sequence (−6 GCCA/GCCAUGG+4) should be included in vertebrate mRNAs located around the initiator codon (M, 1997). It has also been suggested that efficient translation is obtained when the −3 position contains a purine base or, in the absence of a purine base, a guanine is positioned at +4 (M, 1997). Prokaryotic genes and some eukaryotic genes do not possess Kozak sequences. Therefore, the expression level of these genes might be increased by the insertion of a Kozak sequence.

The presence of a TPA signal sequence facilitates the secretion of the antigens from the host cells. Consequently, the enhanced protection seen for these TPA-positive plasmids may result from their capacity to induce higher concentrations of other critical cytokines or chemokines (Flynn, 1995).

Adhesion molecules may also serve as potent candidates for immunomodulation by co-injection of the respective genes together with plasmid DNA (J J, 1999). Intracellular adhesion molecule-1 (ICAM-1), lymphocyte function associated-3 (IA-3), and vascular cell adhesion molecule-1 (VCAM-1) along with DNA immunogens have been used for immunomodulation. Antigen-specific lymphoproliferation and cytotoxic responses were enhanced by co-expression of ICAM-1 and LA-3.

Yet another strategy for deliberately modulating intracellular events was the co-delivery of ubiquitin in the form of a fusion protein. In contrast to the effects induced by the leader sequences, tagging proteins with this or similar sequences accelerates and increases the proteasomal degradation. While this approach will improve the induction of CTL responses it will also drastically decrease the antibody response (Fu T M, 1998).

DNA Vaccination Based on the CSP

DNA vaccination based on the circumsporozoite protein (CSP) gene is sufficient to protect at least 90% of BALB/c (Elke S. Bergmann-Leitner, 2005) and C57BL/6 mice against Plasmodium berghei sporozoite infection. This protection depends on epidermal injection of plasmid DNA with a gene gun (Leitner W W, 1997), immunization intervals that optimize the induction of Th2-type immunity (Weiss, 2000), and removal of the glycosyl-phosphatidylinositol (GPI) signal sequence to allow protein secretion (Scheiblhofer, 2001). By applying these principles, researchers are able to protect at least 90% of vaccinated mice against sporozoite challenge following two or three immunizations with the DNA vaccine CSP(−A). Of greater value would be a regimen that induces protective immunity after a single immunization. For a malaria vaccine to be useful in the field, protection against infection needs to be provided after a minimum number of immunizations, optimally a single delivery.

DNA Vaccination Using C3d

A variety of factors and signals initiate and enhance B cell APC function and thus represent potential adjuvants. Among these is C3d, which is generated from C3 during complement activation, and binds to complement receptor 2 (CR2, CD21) on mature B cells. C3d-mediated B cell activation occurs as a consequence of simultaneous engagement of the antigen-specific surface-bound Ig and CD21 by antigen/C3d complexes (Tsokos, 1990). It has been demonstrated, that as an adjuvant, C3d can also function independently of CD21/CD35 (Haas, 2004).

The cleavage of the third complement protein, C3, that is mediated by the C3 convertases of the classical or alternative pathways of complement activation A is the most critical reaction in the complement system (Weis, 1984). The major cleavage fragment, C3b, covalently attaches to the antigen-antibody complex or bacterium bearing the C3 convertase by a transacylation reaction involving the glutamyl component of an internal thiolester (Weis, 1984). This C3b may then be hydrolyzed by factor I in the presence of cofactors to yield sequentially iC3b and C3d,g, which remain attached to the target via the covalent binding site. C3d,g is susceptible to further proteolysis by noncomplement-derived enzymes such as trypsin and neutrophil elastase to generate the C3d fragment (Lachman, 1982).

These proteolytically generated fragments of C3 mediate the binding of complement-activating complexes to various cell types involved in immune and inflammatory reactions by interacting with three types of cellular receptors. The C3b receptor, also termed CR1, has primary specificity for C3b but may also bind iC3b and C4b, the major cleavage fragment of C4, and is present on erythrocytes, neutrophils, monocytes/macrophages, B cells, some T cells, and glomerular podocytes (Weis, 1984). CR1 has been shown to be a membrane glycoprotein having two allotypic forms of 250,000 Mr and 260,000 Mr. A receptor for iC3b, known as CR3, binds this cleavage fragment of C3 and possibly C3d,g and is expressed by neutrophils, monocytes/macrophages, and large, granular lymphocytes having natural killing and antibody-dependent cell-mediated cytotoxic activity (Carlo, 1979). CR3 has been identified as a glycoprotein having two polypeptide chains of 185,000 Mr and 105,000 Mr, respectively (Wright, 1983). An additional type of receptor, designated the C3d receptor or CR2, binds the C3d region of iC3b and C3d,g and is found only on B lymphocytes and certain B-cell lines, such as the Burkitt lymphoma line Raji (Ross G. R., 1973).

C3d expresses an antigenic determinant, detectable by monoclonal antibody (mAb) 130 which is also expressed by iC3b and C3dg but not by C3 or C3b (Tamerius, 1985). Thus, both the CR2 binding site and the neoantigenic site detected by mAb 130 are located in C3d, which also contains the site for covalent binding of membrane and which remains bound to the target cell or particle after removal of C3c by factor I.

Fusion of two or three tandem copies of C3d to recombinant hen egg lysozyme (HEL) has been shown to enhance dramatically the immune response to HEL (Dempsey, 1996). This approach was subsequently used successfully to enhance the efficacy of DNA vaccines. Indeed, constructs encoding genes for pathogen-derived antigens linked in tandem to sequences encoding for C3d delivered more protective immune response than constructs without the C3d (Elke S. Bergmann-Leitner, 2005).

The potential adjuvant effect of C3d in a DNA vaccine against P. berghei malaria was studied using a previously established CSP-based DNA vaccine known as CSP(−A) (Elke S. Bergmann-Leitner, 2005). Paradoxically, a significant reduction of protection against a challenge with sporozoites when two copies of C3d were attached to the CSP(−A) gene was observed, even after three immunizations. It has been determined that C3d associates with the C-terminus of CSP, shifts the immune response to a Th1-type response, limits the humoral response against C-terminal epitopes and significantly reduces protection against P. berghei infection (Elke S. Bergmann-Leitner, 2005). Therefore, the fusion of antigens to C3d is not a generally applicable adjuvant strategy.

It is known generally that the production of high molecular weight polypeptides containing multiple repeating sequences is difficult because of the tendency of repeated DNA sequences to undergo rearrangement during replication. Some of the limitations on internal repetitiveness in plasmids have been discussed by Gupta (Bio/Technology 1. 602-609, 1983). Ferrari et al (U.S. Pat. No. 5,641,648) have described methods for expression of repetitive sequences using synthetic genes constructed from monomeric units which are concatenated by ligation. DNA sequences encoding the same repeated amino acid sequence but differing in nucleotide sequence either within or between monomers were constructed by exploiting the redundancy of the genetic code. The resulting lack of precise repetitiveness at the nucleotide level reduced homologous recombination to the point where the repeated oligopeptide sequence could be expressed. The work of Ferrari et al was restricted to relatively short repeating units of 4 to 30 codons (amino-acids) repeated a large number of times (typically about 30-fold).

Using p28 of the CR2 Binding Motif of C3d as a Molecular Aduvant

Complement fragment C3d fused to hen egg lysozyme has been shown to generate a robust antibody response (Dempsey, 1996). It was proposed that direct targeting of the fusion protein to the complement receptor 2 (CR2) was responsible for the observed effect. Recent reports have indicated that enhancement of the immune response by C3d containing immunogen constructs is accomplished by additional pathways because C3d can act as adjuvant even in the absence of CD21/CD35 (Haas, 2004). Using C3d as a fusion partner, we had sought to further improve the efficacy of a malaria DNA vaccine encoding the major surface antigen of *Plasmodium berghei*, circumsporozoite surface antigen (CSP). Unexpectedly, however, immunization with this construct led to loss of protective immunity (Elke S. Bergmann-Leitner, 2005). In addition, immunization with CSP-C3d led to abrogation of the antibody response against the C-terminus of CSP, a shift in the T cell response from Th2 to Th1-type responses and impaired affinity maturation of antibodies specific for CSP. Because we found that C3d binds to the C-terminus of the CSP (Elke S. Bergmann-Leitner, 2005), we considered binding of C3d to CSP to represent an immune escape mechanism whereby sporozoites may evade the production of protective antibody.

In an effort to take advantage of the reported adjuvant potential of C3d, while avoiding a binding of the C3d-adjuvanted protein to immunogenic regions of CSP, we decided to use the CR2 binding motif of C3d, known as p28, as a molecular adjuvant to CSP which, in theory, should provide the immune-enhancing effects of CR2-biding without masking immunogenic regions of CSP. p28 tetramers have been shown before to enhance the anti-Ig-induced B cell response (Tsokos, 1990). We demonstrated that immunization of mice with CSP-3 p28 DNA constructs provides better protection than CSP alone constructs 6 weeks after the 2nd boost and this protection is associated with better IgG1 anti-*P. berghei* antibody production and absence of IgG2a anti-*P. berghei* antibody. In contrast, immunization with CSP-3 C3d DNA constructs resulted in limited protection, failure to produce IgG1 antibody and robust production of IgG2a antibody. Therefore, use of p28 rather the full length C3d may serve as a more reliable molecular adjuvant.

Characterization of p28

CR2 is a 140-kDa glycoprotein that specifically binds iC3b, C3dg. and C3d fragments of C3 and the EBV envelope protein gp350/220 (Tsokos, 1990). CR2 is expressed primarily by B cells, although it has been found on other cell types (Tsokos, 1990).

CR2 binds a site on C3 that is composed of residues 1205-1124 of the C3 sequence (JOHN D. LAMBRIS, 1985). Synthetic C3 peptides P14 (residues 1201-1214) and P28 (residues 1187-1247) bind to CR2 (JOHN D. LAMBRIS, 1985) and can be used as ligands in functional assays. A number of murine mAb that bind human CR2, including the murinem Ab HB5, have been produced (Ross G. a., 1985).

CR2 has been considered to play a role in B cell differentiation and proliferation. Polyclonal and monoclonal antibodies to CR2 as well as particle bound C3d have been shown to enhance B cell responses in different systems (Tsokos, 1990). P14 and P28 peptides inhibit the maturation of murine B cell progenitors (Gisler, 1988) while they support the growth of CR2-binding EBV lymphoblastoid B cell lines (Servic, 1989).

Despite all efforts to generate a vaccine that induces an immune response against a malaria antigenic determinant and protects from illnesses caused by the malaria parasite, many vaccines do not fulfill all requirements as described above. Whereas some vaccines fail to give a protective efficiency of over 85% in vaccinated individuals, others perform poorly in areas, such as, production or delivery to the correct cells of the host immune system.

Therefore, there exists a need for a more reliable molecular adjuvant for DNA vaccinations against Malaria.

SUMMARY OF THE INVENTION

Complement fragment C3d fused to hen egg lysozyme has been shown to generate a robust antibody response (Dempsey, 1996). It was proposed that direct targeting of the fusion protein to the complement receptor 2 (CR2) was responsible for the observed effect. Recent reports have indicated that enhancement of the immune response by C3d containing immunogen constructs is accomplished by additional pathways because C3d can act as adjuvant even in the absence of CD21/CD35 (Haas, 2004). C3d has been used in numerous disease models with varying success (reviewed in (Bermann-Leitner E S, 2006)). Using C3d as a fusion partner, we had sought to further improve the efficacy of a malaria DNA vaccine encoding the major surface antigen of *Plasmodium berghei*, circumsporozoite surface antigen (CSP). Unexpectedly, however, immunization with this construct led to loss of protective immunity (Elke S. Bergmann-Leitner, 2005). In addition, immunization with CSP—C3d led to abrogation of the antibody response against the C-terminus of CSP, a shift in the T cell response from Th2 to Th1-type responses and impaired affinity maturation of antibodies specific for CSP. Because we found that C3d binds to the C-terminus of the CSP, we considered binding of C3d to CSP to represent an immune escape mechanism whereby sporozoites may evade the production of protective antibody.

In an effort to take advantage of the reported adjuvant potential of C3d, while avoiding a binding of the C3d-adjuvanted protein to immunogenic regions of CSP, we decided to use the CR2 binding motif of C3d, known as p28, as a molecular adjuvant to CSP which, in theory, should provide the immune-enhancing effects of CR2-biding without masking immunogenic regions of CSP. p28 tetramers have been shown before to enhance the anti Ig-induced B cell response (Scheiblhofer, 2001). We demonstrate here that immunization of mice with CSP-3 p28 DNA constructs provides better protection than CSP alone constructs 6 weeks after the 2nd boost and this protection is associated with better IgG1 anti-*P. berghei* antibody production and absence of IgG2a anti-*P. berghei* antibody. In contrast, immunization with CSP-3 C3d DNA constructs resulted in limited protection, failure to produce IgG1 antibody and robust production of IgG2a antibody. Therefore, use of p28 rather the full length C3d may serve as a more reliable molecular adjuvant.

The various features of novelty that characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 2: A table showing that C3d limits the protective efficacy of CSP(-A) against *Plasmodium berghei*.

FIG. 5: A table showing that CSP-3p28 induces more robust protection compared to CSP(-A) when mice are rechallenged.

DESCRIPTION OF THE PREFERRED EMBODIMENTS

Figure 1:
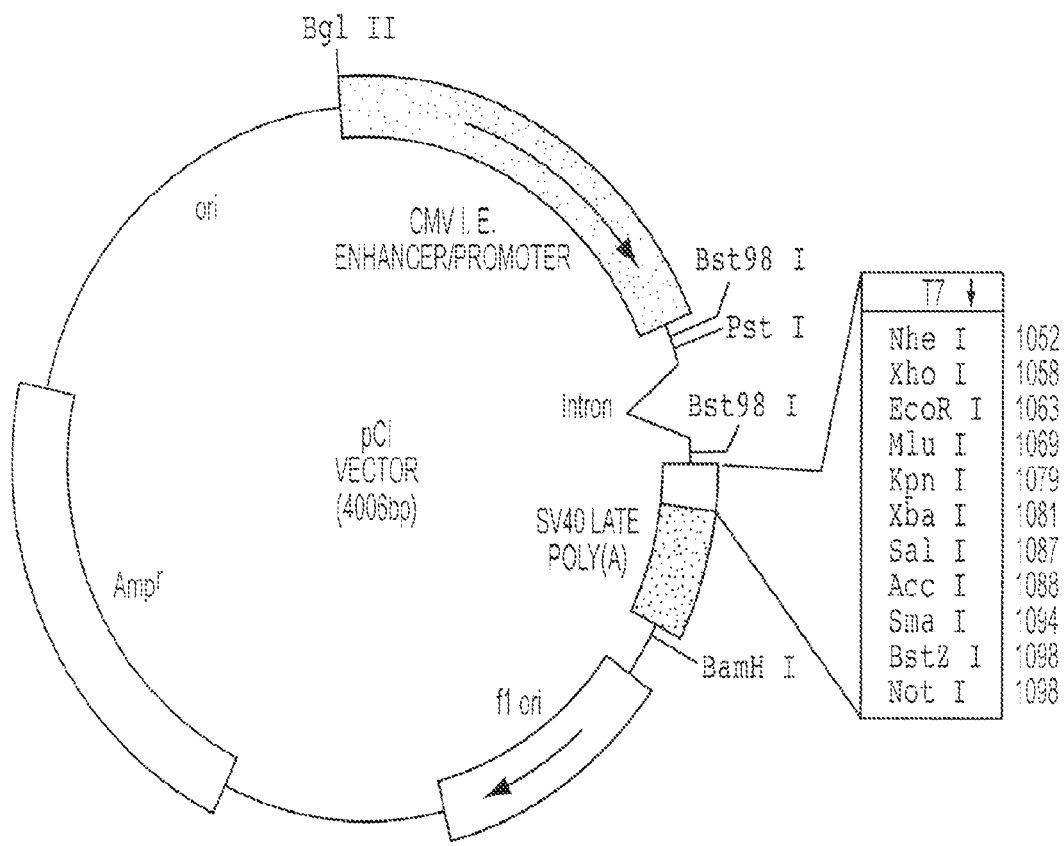
FIG. 1: A vector map of the pCI Mammalian expression plasmid.

The practice of the present invention will employ, unless otherwise indicated, conventional methods of chemistry, biochemistry, recombinant DNA techniques and immunology, within the skill of the art. Such techniques are explained fully in the literature. See, e.g., Sambrook, et al., Molecular Cloning: A Laboratory Manual (2nd Edition); Methods In Enzymology (S. Colowick and N. Kaplan eds., Academic Press, Inc.); DNA Cloning, Vols. I and II (D. N. Glover ed.); Oligonucleotide Synthesis (M. J. Gait ed.); Nucleic Acid Hybridization (B. D. Hames & S. J. Higgins eds.); Animal Cell Culture (R. K. Freshney ed.); Perbal, B., A Practical Guide to Molecular Cloning.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to an antigen includes a mixture of two or more antigens, and the like.

The following amino acid abbreviations are used throughout the text:

Alanine: Ala (A) Arginine: Arg (R) Asparagine: Asn (N) Aspartic acid: Asp (D) Cysteine: Cys (C) Glutamine: Gln (O) Glutamic acid; Glu (E) Glycine; Gly (G) Histidine: His (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V)

DEFINITIONS

In describing the present invention, the following terms will be employed, and are intended to be defined as indicated below.

By Intron A fragment is meant a fragment derived from an Intron A sequence of a CMV immediate-early enhancer/promoter region, which does not include the entire Intron A sequence.

The terms polypeptide and protein refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like.

For purposes of the present invention, the polypeptide expressed by the coding sequence may be one useful in a vaccine, therapeutic or diagnostic and may be derived from any of several known viruses, bacteria, parasites and fungi, as well as any of the various tumor antigens. Alternatively, the expressed polypeptide may be a therapeutic hormone, a transcription or translation mediator, an enzyme, an intermediate in a metabolic pathway, an immunomodulator, and the like.

Furthermore, for purposes of the present invention, a polypeptide refers to a protein which includes modifications, such as deletions, additions and substitutions (generally conservative in nature), to the native sequence, so long as the protein maintains the desired activity. These modifications may be deliberate, as through site-directed mutagenesis, or may be serendipitous, such as through mutations of hosts which produce the proteins or errors due to PCR amplification.

A coding sequence or a sequence which encodes a selected polypeptide, is a nucleic acid molecule which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral (e.g. DNA viruses and retroviruses) or procaryotic DNA, and synthetic DNA sequences. A transcription termination sequence may be located 3' to the coding sequence.

A nucleic acid molecule can include both double- and single-stranded sequences and refers to, but is not limited to, cDNA from viral, procaryotic or eucaryotic mRNA, genomic DNA sequences from viral (e.g. DNA viruses and retroviruses) or procaryotic DNA, and especially synthetic DNA sequences. The term also captures sequences that include any of the known base analogs of DNA and RNA.

Operably linked refers to an arrangement of elements wherein the components so described are configured so as to perform their desired function. Thus, a given promoter operably linked to a coding sequence is capable of effecting the expression of the coding sequence when the proper transcription factors, etc., are present. The promoter need not be contiguous with the coding sequence, so long as it functions to direct the expression thereof. Thus, for example, intervening untranslated yet transcribed sequences can be present between the promoter sequence and the coding sequence, as can transcribed introns, and the promoter sequence can still be considered operably linked to the coding sequence.

Recombinant as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term recombinant as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

A control element refers to a polynucleotide sequence which aids in the expression of a coding sequence to which it is linked. The term includes promoters, transcription termination sequences, upstream regulatory domains, polyadenylation signals, untranslated regions, including 5'-UTRs (such as Exon 2 of the hCMV enhancer/promoter region 5'-UTR) and 3'-UTRs and when appropriate, leader sequences and enhancers, which collectively provide for the transcription and translation of a coding sequence in a host cell.

A promoter as used herein is a DNA regulatory region capable of binding RNA polymerase in a host cell and initiating transcription of a downstream (3' direction) coding sequence operably linked thereto. For purposes of the present invention, a promoter sequence includes the minimum number of bases or elements necessary to initiate transcription of a gene of interest at levels detectable above background. Within the promoter sequence is a transcription initiation site, as well as protein binding domains (consensus sequences) responsible for the binding of RNA polymerase. Eucaryotic promoters will often, but not always, contain 1 TATAA boxes and CAAT boxes.

A control sequence directs the transcription of a coding sequence in a cell when RNA polymerase will bind the promoter sequence and transcribe the coding sequence into mRNA, which is then translated into the polypeptide encoded by the coding sequence.

A host cell is a cell which has been transformed, or is capable of transformation, by an exogenous DNA sequence.

A heterologous region of a DNA construct is an identifiable segment of DNA within or attached to another DNA molecule that is not found in association with the other molecule in nature. For example, a sequence encoding a human protein other than the immediate-early 72,000 molecular weight protein of hCMV is considered a heterologous sequence when linked to an hCMV IE1 enhancer/promoter. Similarly, a sequence encoding the immediate-early 72,000 molecular weight protein of hCMV will be considered heterologous when linked to an hCMV promoter with which it is not normally associated. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

By selectable marker is meant a gene which confers a phenotype on a cell expressing the marker, such that the cell can be identified under appropriate conditions. Generally, a selectable marker allows selection of transected cells based on their ability to thrive in the presence or absence of a chemical or other agent that inhibits an essential cell function. Suitable markers, therefore, include genes coding for proteins which confer drug resistance or sensitivity thereto, impart color to, or change the antigenic characteristics of those cells transfected with a nucleic acid element containing the selectable marker when the cells are grown in an appropriate selective medium. For example, selectable markers include: cytotoxic markers and drug resistance markers, whereby cells are selected by their ability to grow on media containing one or more of the cytotoxins or drugs; auxotrophic markers by which cells are selected by their ability to grow on defined media with or without particular nutrients or supplements, such as thymidine and hypoxanthine; metabolic markers by which cells are selected for, e.g., their ability to grow on defined media containing the appropriate sugar as the sole carbon source, or markers which confer the ability of cells to form colored colonies on chromogenic substrates or cause cells to fluoresce. Representative selectable markers are described in more detail below.

Expression cassette or expression construct or construct refers to an assembly which is capable of directing the expression of the sequence(s) or gene(s) of interest. The expression cassette includes control elements, as described above, such as a promoter or promoter/enhancer (such as the hCMV IE1 enhancer/promoter) which is operably linked to (so as to direct transcription of) the sequence(s) or gene(s) of interest, and often includes a polyadenylation sequence as well. An expression cassette will also include an Intron A fragment as defined above and, optionally, Exon 2 of the hCMV IE1 enhancer/promoter region. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a mammalian origin of replication (e.g., a SV40 or adenovirus origin of replication).

Transformation, as used herein, refers to the insertion of an exogenous polynucleotide into a host cell, irrespective of the method used for insertion: for example, transformation by direct uptake, transfection, infection, and the like. For particular methods of transfection, see further below. The exogenous polynucleotide may be maintained as a nonintegrated vector, for example, an episome, or alternatively, may be integrated into the host genome.

By isolated is meant, when referring to a polypeptide, that the indicated molecule is separate and discrete from the whole organism with which the molecule is found in nature or is present in the substantial absence of other biological macro-molecules of the same type. The term isolated with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

Homology refers to the percent identity between two polynucleotide or two polypeptide moieties. Two DNA, or two polypeptide sequences are substantially homologous to each other when the sequences exhibit at least about 50%, preferably at least about 75%, more preferably at least about 80%-85% (80, 81, 82, 83, 84, 85%), preferably at least about 90%, and most preferably at least about 95%-98% (95, 96, 97, 98%), or more, or any integer within the range of 50% to 100%, sequence identity over a defined length of the molecules. As used herein, substantially homologous also refers to sequences showing complete identity to the specified DNA or polypeptide sequence.

Identity refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the Match value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, COS cells, HeLa cells, baby hamster kidney cells and many others. A common, preferred bacterial host is $E.\ coli$.

Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, eds. Ausubel et al., John Wiley & Sons, 1992. Transformation procedures depend on the host used, but are well known.

Nucleic acid for use according to the invention may be DNA or RNA, and may be single-stranded or double-stranded, cDNA, genomic DNA or wholly or partially synthetic. Double-stranded DNA is preferred.

The nucleotide sequence and predicted amino acid sequence of mouse C3d are disclosed in Domdey et al. (1982) PNAS USA 79: 7619-7623 and Fey et al (1983) Ann. N.Y. Acad. Sci. 421: 307-312). The nucleotide sequence and predicted amino acid sequence for human C3d are disclosed in de Bruijn and Fey (1985) PNAS USA 82: 708-712. Nucleic acid encoding C3d from other species may be isolated using the human or mouse sequence information to prepare one or more probes for use in standard hybridization methods. When C3d is to be employed in the invention and administered to a subject, the C3d may be matched to the species to be immunized (e.g. mouse C3d to be used in mouse, human C3d in human and so on). However, experimental evidence is included herein demonstrating species cross-reactivity, at least between mouse and human (e.g. mouse C3d binds to CD21 on human cells, such as human Raji B lymphoblastoid cells), so species matching of C3d and subject may not be essential, even if preferred.

In an embodiment alternative to coupling of antigen/immunogen and p28 by expression as a fusion protein, chemical cross-linking may be employed. Chemically cross-linked refers to covalent linkage through use of a chemical cross-linking agent. A chemical cross-linking agent is chosen that reacts with functional groups on the antigen and ligand (e.g. amino acid side chains or the amino- or carboxy-terminus of a peptide chain) such that upon reaction with the cross-linking agent the antigen and ligand become covalently linked. Moreover, the cross-linking agent may contain a spacer molecule that serves to position properly the p28 and antigen.

A wide variety of bifunctional or polyfunctional cross-linking reagents, both homo- and heterofunctional, are known in the art and are commercially available (e.g. Pierce Chemical Co., Rockford, Ill.). Such cross-linking reagents may be reacted with the antigen and ligand by standard methods (e.g. according to the manufacturers instructions). Following cross-linkage, the antigen-ligand complex may be purified from unreacted antigen and ligand by standard methods (e.g., chromatography, SDS-PAGE and the like). The efficacy of chemically cross-linked compositions in stimulating intracellular signals in B cells (e.g. increased intracellular calcium concentrations) and/or modulating immune responses can be evaluated using assays, e.g. as described herein.

Ligands for use in a chemically-crosslinked composition are as disclosed. A preferred ligand is one or more p28 molecules. P28 for use in a chemically-crosslinked composition may be recombinant p28 (e.g. prepared by expression from encoding nucleic acid) or purified, natural p28. For example, C3 can be purified from plasma (e.g. human plasma) and p28 can be prepared therefrom by digestion as described in (Lambris, 1980).

In another embodiment, antigen and ligand may be co-expressed (i.e. both present) on a surface of a carrier structure. Preferably, the antigen and the ligand are co-expressed on the surface of the carrier structure such that, upon contact with a B cell, the antigen can interact with membrane immunoglobulins (mIg) specific for the antigen on the surface of the B cell and the ligand can interact with the CD21/CD19 complex on the surface of the B cell, where the ligand is preferably a p28 fragment.

The carrier structure used for co-expression of the antigen and the ligand may be a liposome (or similar vesicle-type structures that can carry material on their surface, such as microspheres, polyacryl starch microparticles, microcapsules and the like). Antigens and ligands can be covalently attached to the surface of a liposome or other carrier vesicles by standard methods. For review, see Jones, M. N. (1995) Adv. Colloid. Interface Sci. 54:93-128. See also e.g., Heath, T. D. et al. (1980) Biochim. Biophys. Acta 599:42-62; Heath, T. D. and Martin, F. J. (1986) Chem. Phys. Lipids 40:347-358; Hutchinson, F. J., et al. (1989) Biochim. Biophys. Acta 978: 17-24; Therien, H. M. et al. (1991) Cell. Immunol. 136:402-413; Freide, M., et al. (1993) Anal. Biochem. 211:117-122 (all of which are incorporated by reference herein in their entirety. For stimulation of immune responses to the antigen, use of a liposome or a polyacryl starch microparticle as a carrier structure for the antigen and the ligand may have the additional benefit that the liposome or microparticle itself may have adjuvant activity (or can carry an additional adjuvant, such as the monophosphoryl adjuvant lipid A). For a review, see Alving, C. R. (1995) Immunol. Rev. 145:5-31. See also e.g. Raphael, L. and Tom, B. H. (1984) Clin. Exp. Immunol. 55:1-13; Artursson, P., et al. (1986) J. Pharm. Sci. 75:697-701; Degling, L. and Stjaernkvist, P. (1995) Vaccine 13:629-636; Lachman, L. B., et al. (1995) AIDS Res. Hum. Retrovirus. 11:921-932 (all of which are incorporated in their entirety by reference herein). A preferred liposome formulation for stimulating immune responses may comprise an alum-adsorbed liposome containing lipid A and having an antigen and a CD21 or CD19 ligand bound to the surface of the liposome.

The carrier structure may be a cell. For example, a cell can be transfected with recombinant expression vectors encoding membrane-bound forms of the antigen and the ligand such that expression of the vectors in the cell leads to cell-surface expression of the antigen and the ligand. Surface expression of the antigen can be achieved, for example, by linking a DNA fragment encoding a signal sequence to the 5' end of a DNA encoding the antigen (if the antigen does not itself contain a signal sequence) and linking a DNA fragment encoding a transmembrane domain to the 3' end of the DNA encoding the antigen (if the antigen itself does not contain a transmembrane domain), using standard recombinant DNA techniques. The ligand may be modified similarly to achieve cell-surface expression of the ligand. A high level of expression of the antigen and the ligand may be necessary to achieve cross-linking of both mIg and CD21/CD19 on B cells. Accordingly, recombinant expression vectors utilizing strong regulatory elements (e.g. one or more strong enhancers) may be preferred for expression of the antigen and the ligand on surface of the carrier cell.

The carrier structure may be any vaccine or biological particle for administration, for example in the membrane or on the surface of a virus, on HBsAg particles and so on. Coexpression of the antigen/immunogen and ligand for CD21 or CD19 may follow incorporation of appropriate nucleic acid into the viral genome.

The carrier structure may be a solid support, such as a bead (e.g. agarose, sepharose, polystyrene and the like) or a plate. An antigen and a CD21 or CD19 ligand can be attached to a solid support by standard techniques. For example, chemical cross-linking agents such as those described herein may be used to covalently attach the antigen and the ligand to the solid support.

Administration of a composition according to the invention, such as a (p28)$_n$-antigen conjugate, modulates the immune response of the recipient individual. Accordingly, a further aspect of the present invention provides a method of modulating the immune response of an individual to an antigen/immunogen of interest, the method comprising administration of a composition comprising an antigen/immunogen associated with a ligand of CD21 or CD19, such as a molecule comprising the antigen/immunogen coupled to one or more C3d molecules, as disclosed. Enhancement, augmentation, or increase of the immune response may be achieved by coupling a plurality of C3d molecules to the immunogen. Inhibition, reduction or decrease of the immune response may be achieved by the coupling of one p28 molecule.

The administration may be for a prophylactic purpose (vaccination, e.g. anti-microbial) or therapeutic, e.g in immunotherapy (e.g. anti-microbial or anti-tumour). Vaccination may be used to confer on a subject protective immunity to an antigen.

Instead of administering the conjugate in the case of a peptide or polypeptide DNA encoding a fusion may be administered, in accordance with known techniques. (see e.g. Cohen, J. (1993) Science 259: 1691-1692; Yankauekas, M. A., et al. (1993) DNA Cell Biol. 12: 771-776; Boots, A. M., et al. (1992) Vaccine 10: 119-124; Conry, R. M., et al. (1994) Cancer Res. 54: 1164-1168; Montgomery, D. L., et al. (1993) DNA Cell. Biol. 12: 777-783; Wang, B., et al. (1993) DNA Cell Biol. 12: 799-805; San, H., et al. (1993) Hum. Gene Ther. 4: 781-788; Feigner, J. H., et al. (1994) J. Biol. Chem. 269: 2550-2561; Duzgunes, N. and Feigner, J. H. (1993) Methods Enzymol. 221:303-306; Jiao, S., et al. (1992) Exp. Neurol. 115:400-413) (all of which are incorporated by reference herein in their entirety).

Applications of such administration are discussed above, including raising of antibodies to the immunogen. In a further aspect the invention for instance provides a method of raising an antibody response (obtaining antibodies) to an antigen/immunogen of interest which comprises administration to a mammal of the antigen/immunogen in association with a ligand of CD21 or CD19, e.g. coupled to a plurality of p28 molecules, as disclosed. Generally the mammal may be eg human, mouse, rat, rabbit, horse, goat, sheep or monkey. The purpose of administration may be therapeutic or may be to raise antibodies for later use/manipulation, eg using recombinant techniques such as monoclonal antibody technology and/or bacteriophage display (see eg WO92/01047). Isolation of antibodies and/or antibody-producing cells from the mammal may be accompanied by a step of sacrificing the animal.

In accordance with the present invention antibody production in vitro, e.g. in culture, may be stimulated. For example, B cells specific for an antigen of interest may be cultured with a stimulatory composition of the invention to stimulate production by the B cells of antibody for the antigen of interest. The antibodies produced may be isolated from the culture medium, e.g. by virtue of their binding capability for the antigen.

In a further aspect, the present invention provides a pharmaceutical composition which comprises an antigen/immunogen in association with a ligand of CD21 or CD21, such as a (p28).sub.n-immunogen conjugate, as disclosed.

Pharmaceutical compositions according to the present invention may comprise, in addition to the antigen/immunogen in association with a CD21 or CD19 ligand, e.g. (p28).sub.n-immunogen conjugate, a pharmaceutically acceptable excipient, carrier, vehicle, buffer, stabiliser or other materials well known to those skilled in the art. Such materials should be non-toxic and should not interfere with the efficacy of the active ingredient. The precise nature of the carrier or other material will depend on the route of administration, which will preferably be cutaneous, subcutaneous or intravenous injection, especially subcutaneous.

For parental, intravenous, cutaneous or subcutaneous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Sub-cutaneous injection may be preferred route of administration.

A pharmaceutical composition in accordance with the present invention may comprise one or more additional active ingredients. For example, the composition may contain an additional agent that has immunomodulatory properties, such as a cytokine or (additional) adjuvant.

Another aspect of the present invention provides the use of an antigen/immunogen in association with a CD21 or CD19 ligand, e.g. (p28).sub.n-immunogen, (as disclosed) in the manufacture of a composition or medicament for administration to an individual to modulate the immune response of the individual to the immunogen. The purpose of administration may be to obtain antibodies, as discussed.

The present invention is applicable to a wide variety of antigens. In a preferred embodiment, the antigen is proteinaceous, protein, polypeptide or peptide. In another embodiment the antigen is DNA. The antigen may be lipid. It may be a carbohydrate. Preferred antigens include those from a pathogen (e.g. virus, bacterium, parasite) and tumours (especially tumour-associated antigens or tumour markers). Other preferred antigens are autoantigens. Examples of tumour-associated antigens include carcinoembryonic antigen (CEA), prostate-specific antigen (PSA), muc-1 (Agrawal et al. (1995) Cancer Res. 55: 2257-2261), MART-1 (Kawakami et al (1994) J. Exp. Med. 180:347-352) and gp100 (Adema et al (1994) J. Biol. Chem. 269: 20126-20133). Examples of viral antigens include herpes simplex virus-1 proteins such as gB, gC, gD, g EW, gG, gH, gI, gK, gL, Vmw65, ICPO and Icp4, haemagglutinin of a myxovirus (e.g. influenza, mumps or measles) and gp120 of human immunodeficiency virus.

If an antibody or fragment or derivative thereof is employed it must be coupled (e.g. fused) to the antigen or immunogen in a way which retains the ability to bind CD21 or CD19. This may be by fusion with a constant region of a heavy or light chain of an antibody. Fusion at the C-terminus of single chain Fv (scFv) antibody fragments has been shown not to interfere with binding ability of the scFv's. As antibodies can be modified in a number of ways, the term antibody should be construed as covering any specific binding substance having an binding domain with the required specificity. Thus, this term covers antibody fragments, derivatives, functional equivalents and homologues of antibodies, including any polypeptide comprising an immunoglobulin binding domain, whether natural or synthetic. Chimaeric molecules comprising an immunoglobulin binding domain, or equivalent, fused to another polypeptide are therefore included. Cloning and expression of chimaeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) bispecific single chain Fv dimers (PCT/US92/09965) and (ix) diabodies, multivalent or multispecific fragments constructed by gene fusion (WO94/13804; P. Holliger et al Proc. Natl. Acad. Sci. USA 90 6444-6448, 1993).

Antibodies to CD21 have been described and are available in the art (e.g. OKB7, Ortho Pharmaceuticals, Raritan, N.J., USA; and HB-5, American Type Culture Collection, Rockville, Md., USA, No HB 135). Antibodies to CD19 are also available in the art (e.g. Carter et al (1991) J. Immunol. 147: 3663-3671; and Holder et al (1992) Eur. J. Immunol. 22: 2725-2728).

Antibodies which are specific for a target of interest may be obtained using techniques which are standard in the art. Methods of producing antibodies include immunising a mammal (eg mouse, rat, rabbit, horse, goat, sheep or monkey) with the protein or a fragment thereof, or a cell or virus which expresses the protein or fragment. Immunisation with DNA encoding a target polypeptide is also possible. Antibodies may be obtained from immunised animals using any of a variety of techniques known in the art, and screened, preferably using binding of antibody to antigen of interest. For instance, Western blotting techniques or immunoprecipitation may be used (Armitage et al, 1992, Nature 357: 80-82).

As an alternative or supplement to immunizing a mammal, an antibody may be obtained from a recombinantly produced library of expressed immunoglobulin variable domains, eg using lambda bacteriophage or filamentous bacteriophage which display functional immunoglobulin binding domains on their surfaces; for instance see WO92/01047. The library may be naive, that is constructed from sequences obtained from an organism which has not been immunized with the target, or may be one constructed using sequences obtained from an organism which has been exposed to the antigen of interest (or a fragment thereof).

It is possible to take antibodies and use the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma producing a monoclonal antibody may be subject to genetic mutation or other changes, which may or may not alter the binding specificity of antibodies produced.

It may be desirable to humanize non-human (eg murine) antibodies to provide antibodies having the antigen binding properties of the non-human antibody, while minimizing the immunogenic response of the antibodies, e.g. when they are used in human therapy. Thus, humanized antibodies comprise framework regions derived from human immunoglobulins (acceptor antibody) in which residues from one or more complementary determining regions (CDR's) are replaced by residues from CDR's of a non-human species (donor antibody) such as mouse, rat or rabbit antibody having the desired properties, eg specificity, affinity or capacity. Some of the framework residues of the human antibody may also be replaced by corresponding non-human residues, or by residues not present in either donor or acceptor antibodies. These modifications are made to the further refine and optimize the properties of the antibody.

So-called phage display may also be used in humanising antibodies; see e.g. WO93/06213.

Vaccine Constructs

In one embodiment of the invention, the natural endoplasmic reticulum-targeting signal of *P. berghei* CSP is replaced with that from human tissue plasminogen activator (TPA). Furthermore, the putative GPI signal sequence of the CSP is removed to ensure secretion of the encoded proteins. Construction of the CSP plasmid [CSP(−A)] and the empty vector plasmid pcDNA are described in Bergmann-Leitner et al. (Scheiblhofer, 2001).

The murine C3d DNA fragment was amplified by PCR from a plasmid containing the C3 gene, which was a gift from John Lambris (University of Pennsylvania). The forward primer:

```
GGGAGATCTACCCCCGCAGGCTCTGGG      SEQ. ID NO. 1
``` added a unique BglII site at the 5' end and inactivated the thioesterification site by replacing the TGT (Cys) with TCT (Ser). The reverse primer:

```
GGGGATCCGGGGAGGTGGAAGGACACATCC    SEQ ID NO. 2
``` added a unique BamHI site at the 3' end. A precursor plasmid WR65/00/C3d was prepared, ligating the C3d PCR product that was digested with BglII and BamHI, into the WRG6518 vector (Leitner W W, 1997), and the insert was sequenced. A precursor plasmid [pCI-TPA/1C3d(pre)] containing a single copy of C3d was prepared by excising the C3d fragment from WR65/00/1C3d with BamHI and BglII and inserting it into pCI-TPA(-EEF motif) digested with BglII. Adding a second copy of C3d required first inserting a (G4S)2 linker (Dempsey, 1996) into WR65/00/1C3d digested with HindIII and BamHI, generating WR65/00/1C3d+(G4S)2. The two complementary oligonucleotides used to make the linker were:

```
                                           (SEQ. ID NO. 3)
GATCTGGAGGAGGAGGCTCCGGAGGAGGAGGCTCCGGATCCGAATTCA
and
                                           (SEQ. ID NO. 4)
AGCTTGAATTCGGATCCGGAGCCTCCTCCTCCGGAGCCTCCTCCTCCA;
``` they added unique 5' BglII and 3' HindIII sites. The pCI-TPA/3C3d(pre) plasmid, which contains three copies of C3d, was prepared by excising the C3d+(G4S)2 fragment from WR65/00/1C3d+(G4S)2 by digesting with BamHI and BglII and inserting it into pCI-TPA/C3d(pre) digested with BglII, making pCI-TPA/2C3d(pre). This process was repeated from pCI-TPA/2C3d(pre), making pCI-TPA/3C3d(pre). The CS/3C3d chimeric plasmid was created by excising the CSP fragment from the CSP(−A) plasmid with BamHI and inserting it into pCI-TPA/3C3d(pre) digested with BglII. The plasmid used for expressing three tandem copies of C3d (p3C3d) was prepared by cutting pCI-TPA/3C3d(pre) with BamHI and BglII and re-ligating. Plasmids for immunization studies were prepared by Genoquest Inc. (Gaithersburg, Md., USA) using Endo Free Plasmid Giga Kits (Qiagen, Valencia, Calif., USA). Purified plasmid DNA was stored in TE(Tris-EDTA [Ethynelo-Diamine-Tetraacetate]) buffer at −20° C.

Expression of Recombinant CSP in *Escherichia coli* and Protein Purification

The glutathione (GSH)-S-transferase (GST)-fusion expression vector, pGEX-6P, was obtained from Pharmacia. A 48-mer oligonucleotide that codes for six consecutive histidines for nickel chelate affinity chromatography was synthesized containing BamHI and HindIII termini. The pGEX-6P vector was digested with BamHI and HindIII, the oligonucleotide linker was ligated into the expression vector and the reconstructed His-tag-modified pGEX vector was sequenced. The *P. berghei* CSP gene was sub-cloned from the expression vector pCI-TPA/PbCSP using BamHI into the pGEX-His6 vector (3). The PbCSP expression vector was identified as pGST/PbCSP-His. *Escherichia coli* BL21 (DE3) cells were transformed and expression was tested.

Protein was purified using a two-step affinity chromatography method based on GSH-Sepharose 4 Fast Flow (Amersham Pharmacia Biotech AB, Uppsala, Sweden) and Ni+2-nitrilo-tri-acetic acid Superflow (Qiagen). Frozen bacterial cell paste was re-suspended in ice-cold PBS/10 mM dithiothreitol (DTT)/1 mM phenylmethylsulfonylfluoride/0.2 mg/ml lysozyme. The bacterial homogenate was lysed by microfluidization. Following lysis, Triton X-100 was added to 1.0% (v/v final). The lysate was incubated on ice with gentle stirring for 30 min. The Triton X-100-soluble supernatant was collected by centrifugation for 1 h at 15 000 rpm. The GSH-Sepharose resin was prepared by pre-equilibration with PBS/10 mM DTT/1% Triton X-100. Following the application of the soluble supernatant to the column by gravity flow method, the column was washed extensively with equilibration buffer. Protein was eluted with 10 mM GSH, reduced form (Aldrich Chemical, St Louis, Mo., USA), in 50 mM Tris, pH 8.0. The elution peak was dialyzed against PBS/10% glycerol/10 mM imidazole/0.3% Empigen BB (v/v final) (Albright and Wilson, Calbiochem, La Jolla, Calif., USA) at 4° C. overnight. For metal chelate chromatography, Ni+2-NTA resin was pre-equilibrated with PBS/10 mM imidazole/0.3% Empigen BB and the sample was loaded under gravity flow conditions. Following the application of the sample, the column was first washed with PBS/10 mM imidazole/0.3% Empigen followed by a second wash with PBS/0.1% Empigen BB/30 mM imidazole. The recombinant protein was eluted with PBS/500 mM imidazole. The peak fractions were collected and dialyzed against PBS/10% glycerol and stored frozen at −80° C. in aliquots.

Expression of Recombinant CSP N-Terminal and C-Terminal Flanking Regions in *E. coli*

The N-terminal and C-terminal flanking sequences were obtained by PCR amplification from the expression vector, pCI-TPA/PbCSP (Weiss, 2000). The amplification primers for the N-terminal fragment were 5'CSP N-T 1131:

```
5'GTCAGCGGATCCGATGGAC        (SEQ. ID NO. 5)
``` and 3'CSP N-T 1370:

```
                                         (SEQ. ID NO. 6)
5'TGGTGGTGGGGATCCTTGTTTCAATTTATTATTACGCTC
``` and for the C-terminal 5'CSP C-T 1809:

```
                                              (SEQ. ID. NO. 7)
5'CAACCAGGATCCGGTGGTAATAACAATAACAAAAATAATAATGAC
GATTC
``` and 3'CSP C-T 2072:

```
5'TCTTCAGGATCCACTTGAAC       (SEQ. ID NO. 8)
```

Internal BamHI sites are underlined. After amplification, fragments were gel purified, digested with BamHI and ligated to the linearized/dephosphorylated pGex-6P1 vector. The bacterial strain BL21de3 was transformed with each of the vectors, inserts were sequenced and plasmids screened for expression. The clones NT-pGex-6P1 and CT-pGex-6P1 expressed the N-terminal and C-terminal of products of PbCSP, respectively. Recombinant proteins were purified over GSH-Sepharose as described for the full-length recombinant CSP.

Detection of CSP in Transfected Cells

BHK cells American Type Tissue Collection (Rockville, Md., USA) were transfected with 2 µg of an equal mixture of expression plasmid [CSP(–A), CS/2C3d, CS/3C3d, 2C3d or 3C3d] and pcDNA, by using lipofectamine plus (Invitrogen/Life Technologies, Carlsbad, Calif., USA) according to manufacturer's instructions. For flow cytometric assays, secretion was blocked by adding 2 µM brefeldin A (Pharmingen, San Diego, Calif., USA) to the culture for 8 h beginning 18 h after transfection. For western blotting, cells were not treated with brefeldin A and instead, culture supernates containing secreted protein were analyzed. For flow cytometric analysis of protein expression, cells were trypsinized and prepared for intracellular staining by using the Cytofix/cytoperm kit following the manufacturer's instructions (Pharmingen). CSP expression was detected with pooled hyperimmune serum from animals immunized with CSP(–A) by gene gun [isotype control is pooled serum from mice immunized with pcDNA using the same regimen as with CSP(–A)]. C3d expression was determined using a commercially available polyclonal rabbit anti-human C3d antibody (DAKO, Fort Collins, Colo., USA), and normal rabbit IgG was used as isotype control. Affinity-purified, PE-conjugated goat anti-mouse IgG (Southern Biotechnology, Birmingham, Ala., USA) and Spectrared-conjugated goat anti-rabbit IgG were used as second-step reagents. Data were expressed as percent specific positive cells and mean fluorescence intensity of the gated positive cells. For analysis of protein expression by western blot, culture supernatants containing secreted antigen were harvested 24 h after transfection and centrifuged at 100 000 g for 1 h to pellet membrane vesicles. Samples equivalent to 2×105 cells per lane were applied to 4-20% polyacrylamide gel (Invitrogen) and size fractionated by SDS gel electrophoresis (120 V, 90 min). Subsequently, proteins were transferred onto nitrocellulose membranes (25 V, 1 h).

The membranes were blocked in PBS+0.3% Tween-20 for 30 min at room temperature (RT), then incubated with 1:20 000 diluted mAb 4B10 (directly conjugated to HRP, gift from Robert Wirtz, CDC, Atlanta, Ga., USA) for 1 h at RT. After three washes with PBS+0.05% Tween, reactive bands were visualized using enhanced chemiluminescence (ECL) plus and exposing the membranes to photographic film.

Detection of C3d Binding to CSP

BHK cells were transfected with various plasmids (pcDNA, 2C3d or 3C3d) as described above. Secretion was blocked by adding 2 µM brefeldin A to the culture for 8 h beginning 24 h after transfection. Cells were harvested by trypsinization and washed and cell lysates prepared by freeze thawing and brief sonication. To assay for CSP and C3d binding, microtiter wells were treated overnight with 50 ng per well of (i) the C-terminal flanking sequence of CSP (CSP-CT), (ii) the N-terminal flanking sequence of CSP(CSP-NT), (iii) 24-mer peptide representing the repeat region of CSP (repeat region, 50 ng/ml), (iv) recombinant GST/CSP or (v) GST protein (GST, 50 ng/ml) as negative control. Plates were then blocked with PBS+1% BSA for 1 h at RT, then cell lysates from transfected cells were added and incubated overnight at 4° C. Binding of C3d was detected by the anti-C3d antibody (1 µg/ml), followed by goat anti-rabbit antiserum conjugated with alkaline phosphatase (dilution 1:500). After adding the substrate BluePhos (Kirkegaard Perry, Gaithersburg, Md., USA), plates were read at 570 nm.

Immunization

Mice used for immunizations were 6- to 8-week old BALB/c females from the Jackson Laboratory (Bar Harbor, Me., USA). Sera were collected 1 day prior to each immunization and 2 weeks after the last immunization, which was prior to challenge with live *P. berghei* sporozoites. Sera were preserved by adding sodium azide (final concentration, 0.2%) and stored at 4° C. Mice were vaccinated three times at 4-week intervals epidermally with a Helios gene gun (Bio-Rad, Hercules, Calif., USA). Vaccine was prepared by precipitating plasmid DNA onto gold beads (1.6 µm diameter) with CaCl2 in the presence of spermidine at a loading rate of 2 µg DNA mg-1 of gold (1). Mice received a dose of 3 µg of DNA divided between three non-overlapping areas on the shaved abdomen at a helium pressure of 400 psi.

ELISA

Ninety-six-well plates (Immunolon 2 HB, Thermo Labsystems, Franklin, Mass., USA) were coated by overnight incubation with recombinant GST/CSP, the N-terminal part of CSP(CSP-NT), the C-terminal part of CSP(CSP-CT) or a 24-mer peptide (DPPPPNPN)3 representing a CSP repeat epitope at a concentration of 1 µg/ml in PBS at 4° C. Plates were washed with PBS/0.1% Tween-20 using the 96-well plate automatic ELISA-plate washer (Skatron, Sterling, Va., USA) and blocked with blocking buffer (PBS, 1% BSA, pH 7.5) for 1 h at 37° C. Sera were serially diluted in blocking buffer, incubated for 2 h at 37° C. and then washed. Alkaline phosphatase-conjugated goat anti-mouse IgG, IgG1 and IgG2a (all from Southern Biotechnology) detection antibodies were added in blocking buffer (1:1000) and incubated for 1 h at 37° C. The assay was developed with BluePhos substrate (Kirkegaard Perry) for 30 min at RT, then stopped with stopping solution (Kirkegaard Perry) and read at 570 nm. Antibody concentration was determined by establishing a standard curve (run in parallel with each assay) with purified mouse IgG, IgG1 and IgG2a. For each serum, we determined a concentration that was within the linear portion of the reaction curve and used this dilution to extrapolate the actual antibody concentration in the assay wells.

Antibody Avidity Determination by Thiocyanate Elution

Based on their respective antibody titers, serum samples were diluted in blocking buffer to obtain comparable concentrations of IgG, incubated for 2 h at 37° C. and then washed. Antigen-antibody interactions were disrupted by the addition of increasing concentrations of the chaotropic agent sodium thiocyanate (NaSCN) in PBS (0, 0.5, 1, 1.5, 2, 2.5, 3, 4 and 5 M NaSCN) for 15 min (17). Plates were then washed to remove the NaSCN and processed following the standard ELISA protocol. The effective concentration of NaSCN required to release 50% of antiserum (ED50) was determined and used to compare the affinity of the antibody response induced by the vaccines.

ELISA-SPOT Analysis

ELISA-SPOT plates (Millipore, Bedford, Mass., USA) were coated with capturing mAb (Pharmingen, clone R4-6A2 for IFN-{gamma}, clone 11B11 for IL-4, 4 µg/ml) overnight at 4° C. in sterile PBS. Plates were then blocked with PBS+ 1% BSA and later cells were seeded at 105 lymphocytes per well in HL-1 medium (GIBCO/Invitrogen, Carlsbad, Calif., USA). Lymphocytes were obtained by lysing RBCs by osmotic shock (ACK Ammonium Chlorid Potassium (K) lysis buffer, GIBCO/Invitrogen). Cells were stimulated with 20 µg/ml recombinant CSP, peptides CS57-70 (18), CS58-65 (19), CS252-260 (20) and CS252-260 (21) or a mix of these peptides. Plates were incubated for 24 h (IFN-{gamma}) or 48 h (IL-4) before cells were washed out and the biotinylated, detecting mAb was added (Pharmingen, clone XMG1.2 for IFN-{gamma}, clone BVD6-24G2 for IL-4, 2 µg/ml). Detecting mAb was incubated overnight at 4° C. Finally, wells were treated with streptavidin-alkaline phosphatase (Southern Biotechnology; 1:1000 diluted) for 2 h and the assay was developed using nitro-blue tetrazolium chloride/5-Bromo-4-chloro-3'-indoly-phosphate-p-toluidine salt substrate (Pierce). Analysis of the ELISA-SPOT assay plates was done using the C.T.L. imaging system (ImmunoSpot Analyzer, Cellular Technology Ltd, Cleveland, Ohio, USA). The number of spots in wells containing only unstimulated lymphocytes was used as background control. Spots reported from cultures with stimulated lymphocytes were corrected using their corresponding media control.

Magnetic Bead Separation

Single-cell suspensions were prepared and erythrocytes were lysed by using ACK lysis buffer. CD4+ or CD8+ splenocytes were purified using magnetic bead-labeled antibodies (Miltenyi Biotec, Auburn, Calif., USA) according to the manufacturer's instructions. Separation was performed by using the Miltenyi OctoMACS system, which produces a >95% pure population. Cells were then washed with HL-1 medium (Invitrogen), suspended at 1×106 cells/ml and plated at 1×105 cells per well along with 2×105 irradiated APC per well (splenocytes from naive mice, irradiated with 3000 rad). ELISA-SPOT analysis was performed as described above. Wells containing only irradiated APC and antigen were set up to ensure that the APC did not produce any cytokines.

Construction of CSP+A and CSP−A Plasmid

Creation of the CSP+A and CSP−A plasmids used in these studies required preparation of precursors as follows: pCI plasmid (Promega) (see FIG. 1) was rearranged to remove unique BamHI and BglII sites by digesting with both enzymes, religating the resulting fragment and selecting clones for loss of the BamHI and BglII sites. This rearranged vector, pCI(-BamHI-BglIII), was then digested with XhoI and NotI, and the residual vector was ligated via these sites with an oligonucleotide, which also contained restriction sites for BamHI, AflIII, BglIII and EcoRI, thereby generating pCI(-EEF motif). The ER targeting sequence from human tissue plasminogen activator (hTPA) was obtained from pCMV-hTPA/CSP [20] by digesting with XhoI and BamHI and introduced into pCI(-EFF motif) digested with the same enzymes. The resulting vector was designated pCI-TPA(-EEF motif). A stop codon in frame with hTPA was introduced into this vector via the unique NheI and BglIII sites by using an oligonucleotide pair (FIG. 2, Stop), thus producing the final basic expression plasmid (pCI-TPA, stop,-EEF motif).

The CSP+A plasmid was prepared by subcloning the BamHI fragment from WRG-6518 [18], which contains the CSP gene, into pCI-TPA(stop,-EEF motif), which had been digested with BamHI and BglIII. Preparation of the CSP−A plasmid required several steps. WRG-6518 was digested with PacI and BglIII and ligated with an annealed oligonucleotide pair (FIG. 2, adapters), which introduced an EcoRI site and eliminated the PacI and BglIII sites producing WRG-6618. This plasmid was then digested with BamHI and EcoRI and the fragment was ligated into pCI-TPA(-EEF motif) vector that was recovered after digestion with the same enzymes, thus producing pCI-TPA(PbCSP6618).

The GPI signal was removed from pCI-TPA(PbCSP6618) by replacing the unique AflIII-EcoRI fragment with an equivalent fragment lacking the GPI signal, which was made by PCR (FIG. 2, PCR). This plasmid was identified pCI-TPA (PbCSP6618-A). The final CSP−A expression plasmid for these studies was prepared by ligating fragment from pCI-TPA(PbCSP6618-A) digested with NheI and BamHI into pCI-TPA(stop,-EEF motif) digested with the same enzymes.

The sequences of the constructs were verified using an Abi Prism™ Genetic Analyser (Perkin Elmer, Norwalk, Conn.). The plasmids were propagated in the *Escherichia coli* strain XI1-blue (Stratagene, La Jolla, Calif.) and purified using Endo Free Plasmid Giga Kits (Quiagen, Hilden, Germany) according to the protocol of the manufacturer. Purified plasmid DNA was stored in endotoxin-free H2O at −20° C.

Construction of C3-Derived CR2-Binding Peptides

The p28 fragment of C3d was amplified from pCI-CSP-3xC3d using OAN445:

```
                                          SEQ. ID. NO. 15
AATGCACAGATCTGGAGGCGGCGGTTCAGGAGGCGGCGGTAGCAAGTTTC

TGAACACAGCCAAAG
``` and OAN446:

```
                                          SEQ. ID. NO. 16
     AATGCGAATTCTTAGGATCCGGCGTAGGATGTGGCCTCTA,
``` cut with BglIII/EcoRI and ligated into pAN344, which had been cut with BamHI/EcoRI yielding pAN465 (CSP-G4SG4S-p28-STOP).

As an alternative C3-derived CR2-binding peptide (P14 and Pd28) may be prepared as previously detailed. Four peptides corresponding to amino acids 1209-1236, 1227-1236, 1217-1232, and 1211-1225 of the amino acid sequence of C3 may be synthesized, according to the solid-phase methods of Merrifield (Merrifield, 1963) by use of a BioSearch peptide synthesizer. Peptides with an amidated COOH-terminus were prepared with a p-methylbenzhydrylamine resin (MBNA resin) (Steward, 1976). The derivatized L amino acids used in the synthesis were those recommended by Barany and Merrifield (Barany, 1980). The removal of resin-bound peptide was accomplished with 10 ml of HF and 1 ml of anisole per g of peptide-resin conjugate (Barany, 1980). The peptides were purified by fast protein liquid chromatography (FPLC) on a C8 reversed-phase column (Pharmacia) and analyzed, after hydrolysis, in a Beckman automated amino acid analyzer. (Barany, 1980).

Construction of the WRG-6518 Vector

Expression vector WRG-6501 was prepared from vector pNASSP (Clontech, Palo Alto, Calif.) by inserting the CMV immediate/early promoter upstream of the SV40 mini-intron and removing the *Escherichia coli* P-palactosidase gene, leaving a NotI cloning site. CS-pUC-9, containing genomic DNA encoding ANKA strain *P. berghei* CSP, was a gift from Dr. David Lanar, Department of Immunology, Walter Reed Army Institute of Research. WRG-6514 was prepared by excising the CSP gene from CS-pUC-9 with NdeI and DraI and filling with T4 DNA polymerase and dNTPs. NotI linkers were blunt-ligated to the fragment, which, after NotI digestion, was inserted into the NotI site of WRG-6501. Expression vector pJW-4303 (gift from Dr. James Mullins, University of Washington) contains the signal sequence from human tissue plasminogen activator (TPA), an NheI site in-frame at the 3' end of the signal sequence, and a EamHI site a few bases beyond. For constructing WRG-6518, pJW4303 was digested with NheI and blunt-ended with T4 DNA polymerase.

Custom BamHI Linkers:

(5'-CGGATCCG-3')        SEQ. ID. NO. 17 were added by blunt ligation, and the vector was digested with BamHI to produce two EamHI sticky ends: the 5' one derived from one of the linker sites, and the 3' one derived from the original BamHI site. After digestion. the vector was dephosphorylated with calf intestinal alkaline phosphatase. The *P. berghei* CSP insert was prepared by digesting CS-pUC-9 with PflM1 and NdeI, thus producing a CSP gene fragment without its native signal sequence. The sticky ends of the fragment were blunted with T4 DNA polymerase, and the custom BamHI linkers were ligated. The fragment was digested with BamHI and ligated with the pJW4303 vector.

Construction of the pJW4303 Vector pJW4303 is modeled on vectors described by Chapman et al. (7) and incorporated herein by reference in the entirety. It uses approximately 1,600 nucleotides from the cytomegalovirus immediate-early promoter (nucleotides 458 to 2063; GenBank accession number M60231) to drive transcription and sequences from the bovine growth hormone (nucleotides 2148 to 2325; GenBank accession number M57764) to provide a polyadenylation signal. The vector includes a synthetic mimic of the tissue plasminogen activator (TPA) leader sequence:

SEQ. ID. NO. 18
ATGGATGCAATGAAGAGAGGGCTCTGCTGTGTGCTGCTGCTGTGTGGAGC

AGTCTTCGTTTCGGCTAGC that can be placed in frame with expressed proteins by using an NheI site (underlined in the sequence). Templates used for PCR amplifications included p239SpE39 (SIV239), pAbT4593 (SIV251), and pL/239E/V-3 (SIV316) (Kestler, 1991). The 59 PCR primer was designed to clone env fragments in frame with the tissue plasminogen activator leader by using the NheI site. The 39 primers were designed to introduce stop codons for the production of secreted gp110 (sgp110) or gp130 (sgp130) forms of Env and to facilitate cloning into the BamHI site of pJW4303. The 5' primer used for constructions was japcr19:

SEQ. ID. NO. 19
GTCGCTCCAAGCTTGCTAGCCAATATGTCACAGTCTTTTATGG (the NheI site is underlined). The 3' primer for sgp110 was hkpcr2:

SEQ. ID. NO. 20
CCCGGGATCCctaTGCGGGCGCCAGGCCAATCGGAGTGATCTCTACTAATT
T and that for sgp130 was jw8:

SEQ. ID. NO. 21
CGGGATCCctaTGCGGGCGCCAGGTCAAACCAATTGCC (the BamHI site is underlined and the stop codon is in lowercase in the primer sequences). Amplification was carried out in a 100-μl reaction mixture with 2 μg of purified plasmid, 30 pmol of each primer, and 200 μM deoxynucleoside triphosphates. Five cycles of amplification were used with 10 U of cloned Pfu polymerase in the buffer provided by the manufacturer (Stratagene, La Jolla, Calif.). Each cycle consisted of 94° C. for 45 s, 56° C. for 60 s, and 72° C. for 120 s. Samples were ethanol precipitated, gel purified, digested with NheI and BamHI, and ligated into NheI- and BamHI-digested pJW4303. Control plasmid DNAs consisted of pBC12/CMV (pCMV/control) and pJW4303 without inserts. Vaccine and control plasmids were grown in the HB101 strain of *Escherichia coli* and purified twice on cesium chloride density gradients by standard protocols.

Construction of pCMV-TPA/CS Plasmid

Construction of the expression vector WRG-6518 was reported previously (17). In this vector, the natural CSP signal sequence for *P. berghei* CSP was replaced with the human tissue plasminogen activator (hTPA) signal sequence. The plasmid pCMV-hTPA/CSP was prepared by using PCR to amplify the hTPA/CSP insert in WRG-6518 sense primer:

5'-GGGCTCGAGATGGATGCAATGAAG-3'    SEQ. ID. NO. 22

Antisense Primer:

SEQ. ID. NO. 23
5'-CCCGCGGCCGCTTAATTAAAGAATACTAATACTAAT-3' and the product was cloned into the eukaryotic expression vector pCI (Promega, Madison, Wis.) FIG. 1 via the XhoI and NotI restriction sites within the vector's multiple cloning site. The insert's sequence was verified by using an ABI Prism™ genetic analyzer (Perkin-Elmer, Norwalk, Conn.) and was identical to the CSP gene sequence within WRG-6518. The plasmid was propagated in *Escherichia coli* X11-Blue™ (Stratagene, La Jolla, Calif.). Large-scale purification of the expression vector was conducted with Endo Free Plasmid Giga™ kits (Qiagen, Hilden, Germany) according to the manufacturer's protocol. The plasmid DNA was stored in endotoxin-free $H_2O$ at −20° C.

While a specific embodiment of the invention will be shown and described in detail to illustrate the application of the principles of the invention, it will be understood that the invention may be embodied otherwise without departing from such principles.

EXAMPLE

Immunization

Mice were immunized with the pAN502 plasmid as constructed using the methods described above. Mice used for immunizations were 6- to 8-week-old BALB/c females from the Jackson Laboratory (Bar Harbor, Me.). Sera were collected one day prior to each immunization and two weeks after the last immunization, which was prior to challenge with live *P. berghei* sporozoites. Sera were preserved by adding sodium azide (final concentration: 0.2%) and stored at 4° C. Mice were vaccinated three times at four-week intervals epidermally with a Helios gene gun (Bio-Rad, Hercules, Calif.). Vaccine was prepared by precipitating plasmid DNA onto gold beads (1.6 μm diameter) with CaCl2 in the presence of spermidine at a loading rate of 2 μg DNA/mg of gold (Leitner W W, 1997). Mice received a calculated dose of 3 μg DNA divided between three non-overlapping areas on the shaved abdomen at a helium pressure of 400 psi.

Parasite Challenge

Fourteen days after the final immunization, mice were challenged by subcutaneous inoculation of 4,000 *P. berghei* sporozoites dissected from infected mosquito glands. Infection was determined by the presence of blood stage parasites in Giemsa stained thin blood smears one week after challenge (Elke S. Bergmann-Leitner, 2005). Animals that were not infected at that time were tested again one week later. We used this analysis schedule because animals that are infected with *P. berghei* ANKA strain malaria parasites do not self-cure.

Western Blot Analysis

BHK cells (ATCC, VA) were transfected with 2 μg of plasmid using LIPOFECTAMINE PLUS™ (Invitrogen/Life Technologies, Carlsbad, Calif.) according to manufacturer's instructions. Secretion of CSP was blocked by adding 2 μM brefeldin A to the culture for 8 hours beginning 24 hours after transfection. Cells were harvested by trypsinization, washed and cell lysates prepared by freeze thawing and brief sonication. Samples were loaded onto 4-20% polyacrylamide gels (Invitrogen) and size-fractionated by SDS gel electrophoresis (120V, 90 min). Subsequently, proteins were transferred onto nitrocellulose membranes (25V, 1 hr). The membranes were blocked in PBS+0.3% Tween-20 for 30 min at RT, then incubated with 1:20,000 diluted CSP-specific monoclonal antibody 4B10 (directly conjugated to HRP, gift from Dr. Robert Wirtz, CDC Atlanta) for 1 hr at RT. After three washes with PBS+0.05% Tween, reactive bands were visualized using ECLplus™ and exposing the membranes to an image analyzer (BioRad, Hercules, Calif.).

CSP-3p28 Binding to B Cells 96-well plates (Immunolon 2 HB™, Thermo Labsystems, Franklin, Mass.) were coated with 10 μg/ml anti CD19 mab (1D3) diluted in PBS at 4° C. overnight. Plates were then washed with PBS/0.1% Tween 20 and blocked with PBS+5% BSA for 1 hr at RT. Splenocytes were incubated with cell lysates from BHK cells transfected with either 3C3d (negative control) or CS3C3d (positive control) or CSP-3p28 for 1 hr at RT. Then, splenocytes were added to the anti-CD19 coated ELISA plate (2×106 cells/ml) and incubated for 1 hr at RT. Wells were handwashed using PBS+1% BSA and then 1% paraformaldehyde (Sigma) added as fixative for 15 min. Binding of CS3p28 was visualized by adding the CSP-specific monoclonal antibody 4B10 for 1 hr at RT followed by incubation with the peroxidase substrate TMB™ (Pierce, Rockford, Ill.) and reading the plate OD at 650 nm.

ELISA 96-well plates (Immunolon 2 HB) were coated by overnight incubation with recombinant GST-CSP, the N-terminal part of CSP(CSP-NT), the C-terminal part of CSP(CSP-CT), or a 24-mer peptide:

```
DPPPPNPNDPPPPNPNDPPPPNPN     SEQ. ID. NO. 24
``` representing a CSP repeat epitope at a concentration of 1 μg/ml in PBS at 4° C. The production of these ELISA plate antigens has been previously reported (Elke S. Bergmann-Leitner, 2005). Plates were washed with PBS/0.1% Tween 20 using a 96-well plate automatic ELISA-plate washer (Skatron, Sterling, Va.) and blocked with blocking buffer (PBS, 1% BSA, pH 7.5) for 1 h at 37° C. Sera were serially diluted in blocking buffer, incubated for 2 h at 37° C., and then washed. Alkaline phosphatase-conjugated goat anti-mouse IgG, IgG1 and IgG2a (all from Southern Biotechnology, Birmingham, Ala.) detection antibody was added in blocking buffer (1:1,000) and incubated for 1 h at 37° C. The assay was developed with BluePhos substrate (Kirkegaard Perry, Gaithersburg, Md.) for 30 min at room temperature, then stopped with stopping solution (Kirkegaard Perry) and read at 570 nm. Antibody concentration was determined by establishing a standard curve (run in parallel with each assay) with purified mouse IgG, IgG1 and IgG2a. For each serum, we determined a concentration that was within the linear portion of the reaction curve and used this dilution to extrapolate the actual antibody concentration in the assay wells.

Statistical Analysis

The protective effect of vaccination was evaluated using the Fisher's exact test comparing differences between the empty vector control group and vaccine groups. Statistical significance of the serological data was tested using ANOVA analysis and Student T-tests (two-sided).

Results and Discussion

Figure 3:
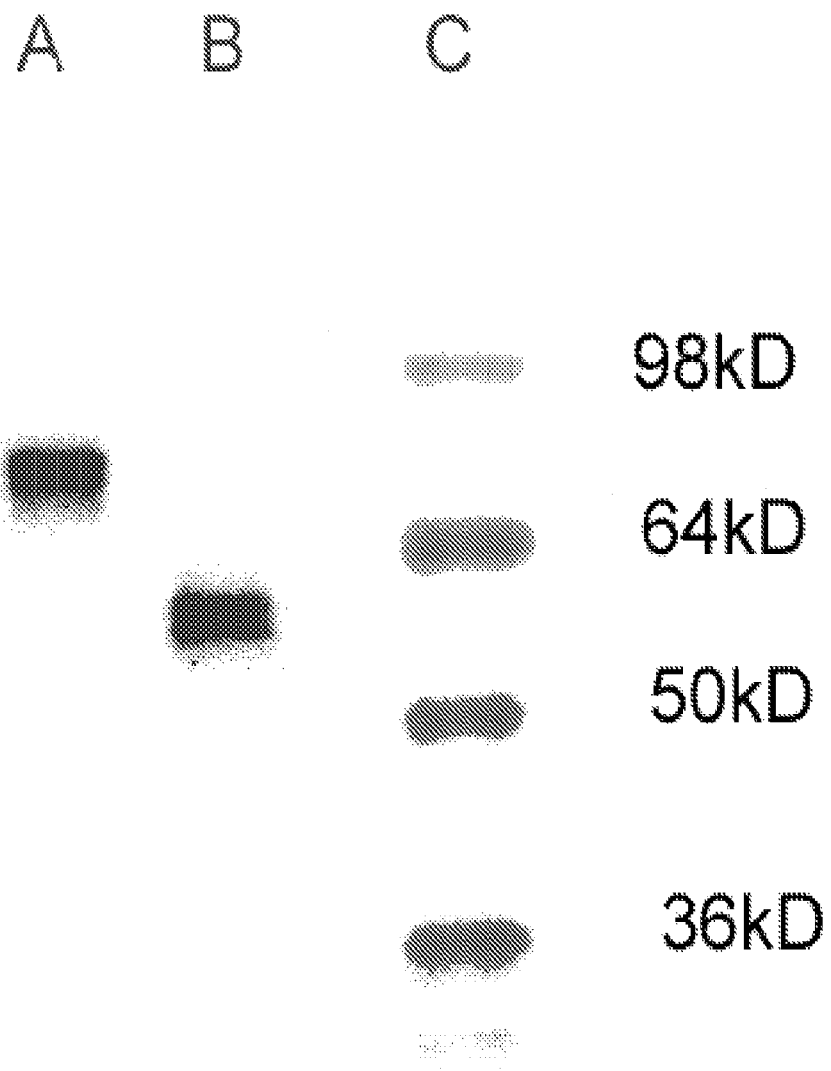
FIG. 3: A photograph of a gel showing the characterization of the CSP-3p28 construct. Immunoblot analysis of cell lysates from transfected BHK cells. 3×104 cells were size fractionated on a 4-20% polyacrylamide gel, and transferred onto nitrocellulose. Lane 1, CSP-3p38, lane 2, CSP(-A), lane 3, Molecular weight marker.

We have previously presented a malaria DNA vaccine encoding the *Plasmodium berghei* CSP protein which can fully protect mice from a lethal malaria challenge when delivered three times by gene gun (Scheiblhofer, 2001). However, a major shortcoming of many malaria vaccines is the failure to induce proper immunological memory making the vaccine only effective for a limited period of time. Our first attempt to improve the efficacy of this vaccine involved the attachment of 3 copies of C3d to CSP. Yet, mice immunized with DNA constructs containing CSP and 3 copies of C3d in tandem were not protected when challenged 3 and 6 weeks after the 2nd boost. The finding that C3d bound to the C-terminus of CSP protein suggested an immune escape mechanism whereby C3d masked important immunogenic regions of CSP. We considered that if we used the CR2-binding region of C3d rather than the whole molecule, we would capitalize on the immune enhancing effects delivered following the engagement of CR2 and avoid unwanted events resulting from the binding of C3d to CSP. We constructed a CSP-based DNA vaccine that contained the full length *P. berghei* CSP without the GPI-anchor sequence (CSP(−A), to ensure expression of a soluble form of the protein, and three copies of the CR2-binding peptide p28 in tandem. To confirm expression of such construct, BHK cells were transfected with either pcDNA, CSP(−A) or CSP-3p28 and treated with Brefeldin A to prevent protein secretion. Cell lysates were harvested and tested by western blotting using an anti-CSP antibody for expression of the transgene. Expression levels of the CSP-3p28 were comparable to the expression of CSP(−A) and the size of the construct was as expected 62 kD (FIG. 3).

Figure 4:
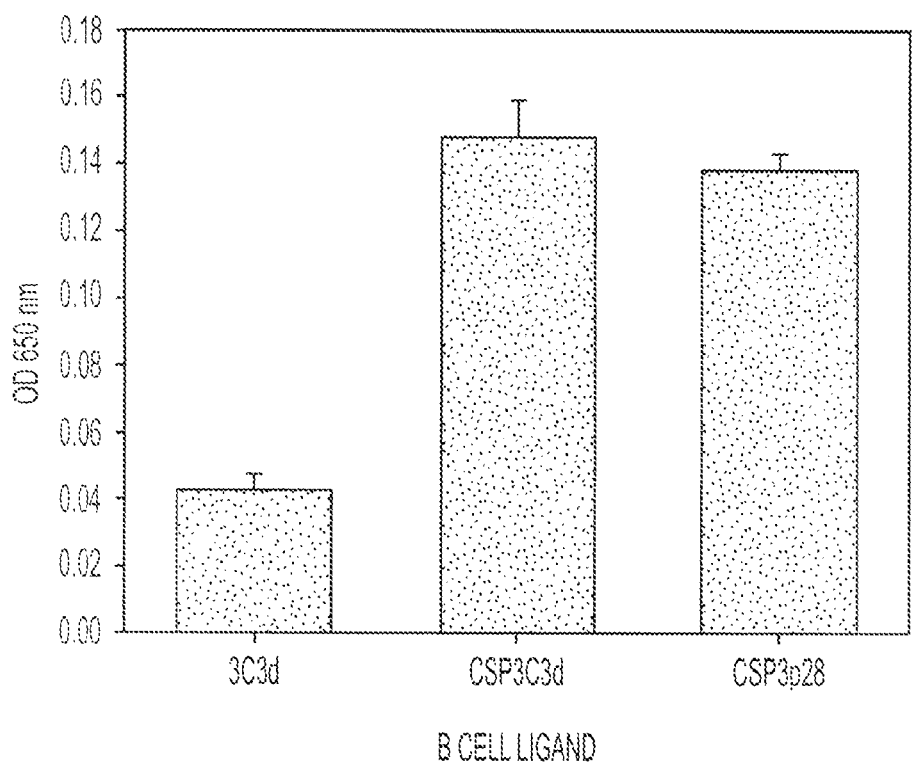
FIG. 4: A bar graph showing the binding of CSP3p28 to B cells. Splenocytes were incubated with lysates of transfected cells which results in the binding of full length ("C3d" or minimal C3d ("p28") to CR2 on B cells. Ligand molecules used: 3C3d (negative control, binds to CR2 but cannot be detected using CSP-specific HRP-labeled monoclonal Ab), CS3C3d (positive control) and experimental CS3p28. Data representative of two independent experiments. Results are expressed as mean and S.E.M. of triplicate cultures.

We next established that the novel fusion-construct, CSP-3p28, produced a protein able to bind to B cells. For this purpose, spleen B cells were immobilized on ELISA plates coated with an anti-CD19 monoclonal antibody after they had been incubated with cell lysates from BHK cells transfected with various constructs (3C3d, CSP3C3d or CSP-3p28). After fixation, binding of CSP-3p28 or CSP3C3d to B cells was visualized with a CSP-specific mAb (4B10) conjugated with HRP. CSP3C3d and CSP-3p28 bound to B cells at comparable levels (FIG. 4). The product of the 3C3d plasmid was not detected with the CSP-specific mAb.

Next we determined the immunogenicity and efficacy of the CSP-3p28 vaccine. The regimen used for the epidermal immunization of mice with the various constructs (pcDNA, CSP(-A), CSP-3p28) included priming with 1 µg of DNA followed by two boosts with equal amount of DNA 4 weeks apart. Two weeks after the third immunization mice were challenged by subcutaneously injecting 4,000 live sporozoites dissected from mosquito salivary glands. Previously we reported that attaching three copies of C3d to the CSP gene results in loss of protective efficacy achieved by immunizing with a plasmid encoding CSP(-A) alone. We had attributed the loss of immunity to the fact that C3d binds to the C-terminus of CSP and prevents the induction of immune responses against this region of the CSP (Elke S. Bergmann-Leitner, 2005). Immunization of mice with CSP-3p28 construct using the same vaccine schedule restored the protective efficacy of CSP plasmid (FIG. 5). More importantly, vaccination with CSP-3p28 resulted in better (100%) protection than CSP alone (60%) against $P.$ $berghei$ sporozoites at the 6 week challenge ($p=0.043$) suggesting that the addition of 3 copies of the p28 peptide to CSP results in the generation of a better vaccine.

Figure 6A:
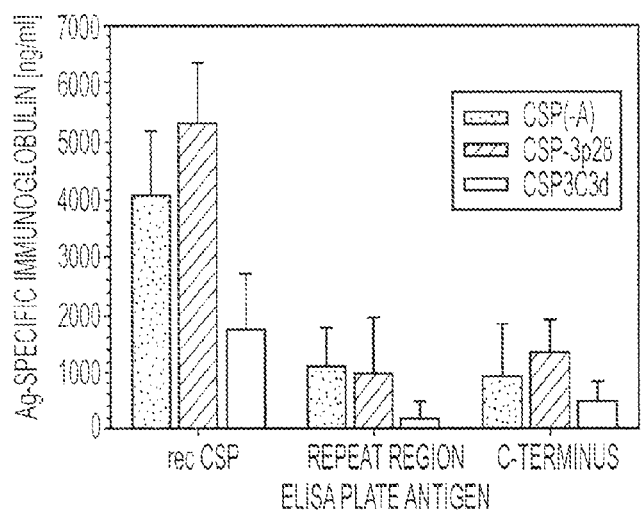
FIG. 6: A bar graph showing that CSP-3p28 restores antibody response to levels achieved by immunization with CSP (-A). Sera (2 weeks after third immunization) were analyzed for fine specificity and isotype profile by ELISA using various plate antigens: panel (A) IgG, panel (B) IgG1, and panel (C) IgG2a. Sera were tested regarding their specificity for the respective plate antigens: full length recombinant CSP protein, a 24-mer peptide representing the repeat region of *Plasmodium berghei*, and the CSP C-terminus. Data expressed as geometric mean (95% Cl) of antibody concentrations of each immunization group (n=10).
Figure 6B:
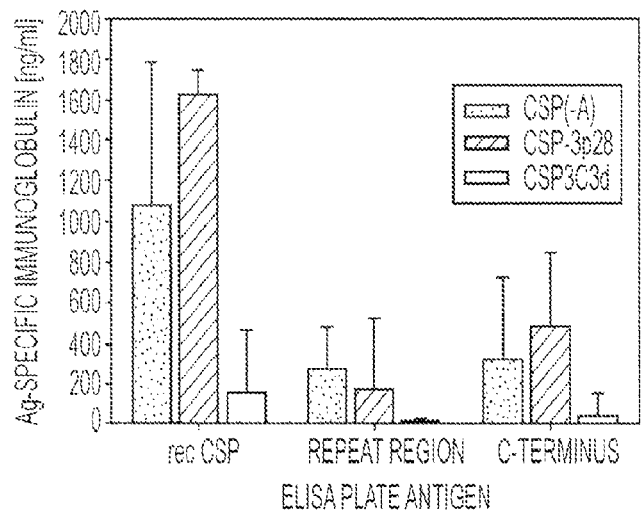
Figure 6C:
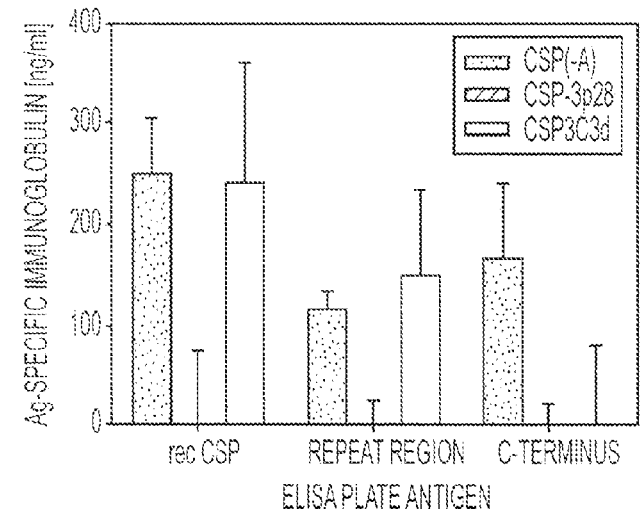

Since we were able to restore protective immunity we sought to determine whether this correlated with the restoration of the antibody response to CSP (FIG. 6). The IgG antibody response to recombinant full length CSP, C-terminus and repeat peptide was comparable in mice immunized with either CSP(-A) or CSP-3p28. As a reference, we re-tested previously generated sera from mice immunized with CSP-3C3d in order to determine quantitative as well as qualitative differences. The amounts of CSP-specific IgG (FIG. 6A) and IgG1 (FIG. 6B) was higher in mice immunized with CSP-3p28 compared to mice immunized with either CSP(-A). As previously reported, the CSP-specific IgG and IgG1 was reduced in mice immunized with CSP-3C3d compared to mice immunized with CSP(-A) (Elke S. Bergmann-Leitner, 2005). IgG and IgG1 antibody levels were significantly higher in mice immunized with CSP(-A) or CSP3-3p38 compared to the levels in mice immunized with CSP-3C3d ($p=0.05$ for IgG and $p=0.031$ for IgG1, Student's 2-sample T-test). In contrast the levels of IgG2a anti-CSP antibody were completely suppressed in mice immunized with CSP-3p28 while they remained intact in mice immunized with CSP-3C3d. The production of IgG2a anti-CSP antibody is associated with lack of protection against $P.$ $berghei$ sporozoites (Elke S. Bergmann-Leitner, 2005).

The most important serological observation was the restoration of the antibody response against the C-terminus of CSP after immunization with CSP3p28 (FIGS. 6A and 6B). Mice immunized with CSP-3p28, unlike mice immunized with CSP-3C3d produced IgG and IgG1 anti-C terminus CSP antibody at levels comparable to those produced in mice immunized with CSP alone. Immunization using CSP-3p28 instead of CSP-3C3d as molecular adjuvant restored the anti-C-terminus specific antibody response ($p=0.025$ for IgG and $p=0.089$ for IgG1 when comparing CSP-3p28 to CSP-3C3d, Student's 2-sample T-test). This observation further supports our previous claim (Elke S. Bergmann-Leitner, 2005) that C3d masks the immunogenic regions of CSP located within the C-terminus of CSP.

Our data demonstrate that p28 may serve as better molecular adjuvant to CSP-based vaccines against malaria. Like C3d, it enables binding to CR2 but does not limit the anti-CSP or anti-C-terminus of CSP IgG and IgG1 antibody response. More importantly, the fact that the CSP-3p28 construct offers better clinical protection at the 6 week challenge with sporozoites than the CSP construct, suggests the generation of better immunological memory. If this proves the case, then this approach may provide insights for future efforts to boost malaria vaccine memory responses.

Sequences Used in Construction of pAN502 Plasmid:
p28 Peptide from C3 Complement Receptor:

```
                                         (SEQ. ID. NO. 25)
Human      1 KFLTTAKDKNRWEDPGKQLYNVEATSYA       28

(SEQ. ID. NO. 26)
Mouse   1209 KFLNTAKDRNRWEEPDQQLYNVEATSYA     1236
```

Use of Mouse p28 for Cloning Behind CSP:

```
Mouse C3d (SEQ. ID. NO. 27):
MGPASGSQLLVLLLLLASSPLALGIPMYSIITPNVLRLESEETIVLEAHD

AQGDIPVTVTVQDFLKRQVLSEKTVLTGASGHLRSVSIKIPASKEFNSDK

EGHKYVTVVANFGETVVEKAVMVSFQSGYLFIQTDKTIYTPGSTVLYRIF

TVDNNLLPVGKTVVILIETPDGIPVKRDILSSNNQHGILPLSWNIPELVN

MGQWKIRAFYEHAPKQIFSAEFEVKEYVLPSFEVRVEPTETFYYIDDPNG

LEVSIIAKFLYGKNVDGTAFVIFGVQDGDKKISLAHSLTRVVIEDGVGDA

VLTRKVLMEGVRPSNADALVGKSLYVSVTVILHSGSDMVEAERSGIPIVT

SPYQIHFTKTPKFFKPAMPFDLMVFVTNPDGSPASKVLVVTQGSNAKALT

QDDGVAKLSINTPNSRQPLTITVRTKKDTLPESRQATKTMEAHPYSTMHN

SNNYLHLSVSRMELKPGDNLNVNFHLRTDPGHEAKIRYYTYLVMNKGKLL

KAGRQVREPGQDLVVLSLPITPEFIPSFRLVAYYTLIGASGQREVVADSV

WVDVKDSCIGTLVVKGDPRDNHLAPGQQTTLRIEGNQGARVGLVAVDKGV

FVLNKKNKLTQSKIWDVVEKADIGCTPGSGKNYAGVFMDAGLAFKTSQGL

QTEQRADLECTKPAARRRSVQLMERRMDKAGQYTDKGLRKCCEDGMRDI

PMRYSCQRRARLITQGENCIKAFIDCCNHITKLREQHRRDHVLGLARSEL

EEDIIPEEDIISRSHFPQSWLWTIEELKEPEKNGISTKVMNIFLKDSITT

WEILAVSLSDKKGICVADPYEIRVMQDFFIDLRLPYSVVRNEQVEIRAVL

FNYREQEELKVRVELLHNPAFCSMATAKNRYFQTIKIPPKSSVAVPYVIV

PLKIGQQEVEVKAAVFNHFISDGVKKTLKVVPEGMRINKTVAIHTLDPEK

LGQGGVQKVDVPAADLSDQVPDTDSETRIILQGSPVVQMAEDAVDGERLK

HLIVTPAGCGEQNMIGMTPTVIAVHYLDQTEQWEKFGIEKRQEALELIKK

GYTQQLAFKQPSSAYAAFNNRPPSTWLTAYVVKVFSLAANLIAIDSHVLC

GAVKWLILEKQKPDGVFQEDGPVIHQEMIGGFRNAKEADVSLTAFVLIAL

QEARDICEGQVNSLPGSINKAGEYIEASYMNLQRPYTVAIAGYALALMNK

LEEPYLGKFLNTAKDRNRWEEPDQQLYNVEATSYALLALLLLKDFDSVPP
```

-continued

VVRWLNEQRYYGGGYGSTQATFMVFQALAQYQTDVPDHKDLNMDVSFHLP

SRSSATTFRLLWENGNLLRSEETKQNEAFSLTAKGKGRGTLSVVAVYHAK

LKSKVTCKKFDLRVSIRPAPETAKKPEEAKNTMFLEICTKYLGDVDATMS

ILDISMMTGFAPDTKDLELLASGVDRYISKYEMNKAFSNKNTLIIYLEKI

SHTEEDCLTFKVHQYFNVGLIQPGSVKVYSYYNLEESCTRFYHPEKDDGM

LSKLCHSEMCRCAEENCFMQQSQEKINLNVRLDKACEPGVDYVYKTELTN

IELLDDFDEYTMTIQQVIKSGSDEVQAGQQRKFISHIKCRNALKLQKGKK

YLMWGLSSDLWGEKPNTSYIIGKDTWVEHWPEAEECQDQKYQKQCEELGA

FTESMVVYGCPN

Amino Acids from CSP which is Inside CSP-3xC3d (SEQ. ID. NO. 28):

AQRNLNELCYNEGNDNKLYHVLNSKNGKIYNRNTVNRLLPMLRRKKNEKK

NEKIERNNKLKQPPPPPNPNDPPPPNPNDPPPPNPNDPPPPNPNDPPPPN

ANDPPPPNANDPAPPNANDPAPPNANDPAPPNANDPAPPNANDPAPPNAN

DPAPPNANDPPPPNPNDPAPPQGNNNNPQPQPRPQPQPQPQPQPQPQPQ

PRPQPQPQPGGNNNNKNNNNDDSYIPSAEKILEFVKQIRDSITEEWSQCN

VTCGSGIRVRKRKGSNKKAEDLTLEDIDTEICKMDKCSSIFNIVSNSLGF

VILLV

Method of Constructing pAN502 Plasmid:

The construction of the full length *P. berghei* CSP without the GPI-anchor sequence CSP(−A) was previously described [6]. For the generation of the CSP-3p28, the C-terminal part of CSP was amplified from pCI-CSP-3xC3d using OAN443:

```
                                        (SEQ. ID. NO. 29)
        AATGCTCTAGAACATGT GGTTCTGGTATAAGAG
``` and OAN444:

```
                                        (SEQ. ID. NO. 30)
    AATGCGAATTCTTAGGATCCACTTGAACATTTATCCATTTTACAA
```

XbaI/EcoRI and ligated into pBLUESCRIPT yielding pAN344. The p28 fragment of C3d was amplified from pCI-CSP-3xC3d using OAN445 (SEQ. ID. NO. 15) and OAN446 (SEQ. ID. NO. 16):
cut with BglII/EcoRI and ligated into pAN344, which had been cut with BamHI/EcoRI yielding pAN465 (CSP-G4SG4S-p28-STOP). The p28 BglII/EcoRI fragment was ligated into pAN465 cut with BamHI/EcoRI yielding pAN485 (CSP-p28-G4SG4S-p28-G4SG4S-p28-STOP). pAN485 was cut with BamHI/EcoRI and ligated to the BglII/EcoRI p28 fragment yielding pAN494 (CSP-G4SG4S-p28-G4SG4S-p28-G4SG4S-p28-STOP). 3xC3d in pCI-CSP-3xC3d was replaced with the AflIIII/EcoRI fragment of pAN494 containing 3xp28 resulting in pAN502. Constructs were verified by sequencing.

The linker described in the production of this plasmid is

```
                                        (SEQ. ID. NO. 31)
        DNA:: GGAGGCGGCGGTTCAGGAGGCGGCGGTAGC
```

```
                                        (SEQ. ID. NO. 32)
        AA: GGGGSGGGGS
```

Human C3 AA (SEQ. ID. NO. 33):
Human C3 NA (SEQ. ID. NO. 34)
Circumsporozoite surface antigen AA (SEQ. ID. NO. 35)
Circumsporozoite surface antigen NA (SEQ. ID. NO. 36)

REFERENCES (The contents of each of which, and the contents of every other publication, including patent publications such as PCT International Patent Publications, being incorporated herein by this reference.)

Aikawa, M. N. (1981). The protective antigen of rodent malarial sporozoites (*Plasmodium berghei*) is a differentiation antigen. *J. Immunol.*, 126:2494-2495.

Aley, S. B. (1986). Synthetic peptides from the circumsporozoite protems of *Plasmodium falciparum* and *Plasmodium knowlesi* recognize the human hepatoma cell line HepG2-A16 in vitro. *J. Exp. Med.*, 164:1918.

Atkinson, C. T. (1989). Expression of *Plasmodium berghei* circumsporozoite antigen on the surface of exoerythrocytic schizonts and merozoites. *Am. J. Trop. Med. Hyg,* 41:9.

Barany, G. M. (1980). *The Peptides*, 2:100-250.

Barry Ma, J. S. (1997). Biological features of genetic immunization. *Vaccine*, 788-791.

Barry MA, J. S. (1997). Biological features of genetic immunization. *Vaccine*, 15:788-91.

Barry, M. A. (1997). Biological features of genetic immunization. 033 *Vaccine*, 15: 788-791.

Berglund P, T. I. (1996). Alphaviruses as vectors for gene delivery. *Trends Biotechnol.*, 14:130-4.

Bermann-Leitner E S, L. W. (2006). Complement 3d: from molecular adjuvant to target of immune escape mechanisms. *Clin. Immunol.*, 121(2):177-85.

Biragyn A, T. K. (1999). Genetic fusion of chemokines to a self tumor antigen induces protective, T-cell dependent antitumor immunity. *Nat. Biotechnol.*, 17:253-8.

Bohm W, K. A. (1996). DNA vector constructs that prime hepatitis B surface antigen-specific cytotoxic T lymphocyte and antibody responses in mice after intramuscular injection. *J Immunol Methods.*, 193:29-40.

Bruna-Romero O., G. G.-A. (2001A). Complete, long-lasting protection against malaria of mice primed and boosted with two distinct viral vectors expressing the same plasmodial antigen. *Proc. Natl. Acad. Sci. U.S.A.* 98, 11491-11496.

Caley I J, B. M. (1997). Humoral, mucosal, and cellular immunity in response to a human immunodeficiency virus type 1 immunogen expressed by a Venezuelan equine encephalitis virus vaccine vector. *J. Virol.*, 71:3031-8.

Caras, I. W. (1991). An internally positioned signal can direct attachment of a glycophospholipid membrane anchor. *J. Cell Biol.*, 113: 77-85.

Carlo, J. R. (1979). *J. Immunol.*, 123:523-528.

Casares S, I. K. (1997). Antigen presentation by dendritic cells after immunization with DNA encoding a major histocompatibility complex class II-restricted viral epitope. *J Exp Med.*, 186:1481-6.

Chapman B S, T. R. (1991). Effect of intron A from human cytomegalovirus (Towne) immediate-early gene on heterologous expression in mammalian cells. *Nucleic Acids Res*, 19:3979-3986.

Chatterjee. S., M. W. (1995). A conserved peptide sequence of the *Plasmodium falciparum* circumsporozoite protein and antipeptide antibodies inhibit *Plasmodium bergher* sporozoite invasion of Hep-G2 cells and protect immunized mice against *P. berghei* sporozoite challenge. *Infect. Immun*, 63:4375.

Chen Y, H. D. (1998). DNA vaccines encoding full-length or truncated Neu induce protective immunity against Neu-expressing mammary tumors. *Cancer Res.*, 58:1965-71.

Ciernik I F, B. J. (1996). Induction of cytotoxic T lymphocytes and antitumor immunity with DNA vaccines expressing single T cell epitopes. *J. Immunol.*, 156:2369-75.

Clyde D. F., H. M. (1973). Immunization of men against sporozoite-induced falciparum malaria. *Am. J. Med. Sci.*, 266:169-177.

Condon C, W. S. (1998). DNA-based immunization by in vivo transfection of dendritic cells. *Nat. Med.*, 2:1122-8.

Cox G J, Z. T. (1993). Bovine herpesvirus 1: immune responses in mice and cattle injected with plasmid DNA. *J. Virol.*, 67:5664-7.

Cross, G. A. (1990). Glycolipid anchoring of plasma membrane proteins. *Annu. Rev. Cell. Biol*, 6: 1-39.

Damem. (1984). Structure of the gene encoding the immunodominant surface antigen on the sporozite of the human malaria parasite *Plasmodium falciparum. Science*, 225: 593-599.

Danko I, W. P. (1997). High expression of naked plasmid DNA in muscles of young rodents. *Hum Mol. Genet.*, 6:1435-43.

Davis H L, M. C. (1997). Immune-mediated destruction of transfected muscle fibers after direct gene transfer with antigen-expressing plasmid DNA. *Gene Ther*, 4:181-8.

Degano P, S. D. (1998). Intradermal DNA immunization of mice against influenza A virus using the novel PowderJect system. *Vaccine.*, 16:394-8.

Dempsey, P. W. (1996). C3d of complement as a molecular adjuvant: bridging innate and acquired immunity. *Science*, 271:348.

Egan, J. E. (1987). Efficacy of murine malaria sporozoite vaccines: implications for human vaccine development. *Science*, 236:453.

Elke S. Bergmann-Leitner, S. S. (2005). C3d binding to the circumsporozoite protein carboxy-terminus deviates immunity against malaria. *International Immunology*, 17(3):245-255.

Fearon D T, C. R. (1995). The C19/CR2/TAPA-1 complex of B lymphocytes: linking natural to acquired immunity. *Annu Rev. Immunol.*, 13:127-149.

Flynn, J. L. (1995). Tumor necrosis factor-alpha is required in the protective immune response against *Mycobacterium tuberculosis* in mice. *Immunity*, 2:561-572.

Forms, X. E. (1999). DNA immunization of mice and macaques with plasmids encoding hepatitis C virus envelope E2 protein expressed intracellularly and on the cell surface. *Vaccine*, 17: 1992-2002.

Fu T M, G. L. (1998). Induction of MHC class 1-restricted CTL response by DNA immunization with ubiquitin-influenza virus nucleoprotein fusion antigens. *Vaccine*, 16:1711-1717.

Gisler, R. C. (1988). Functional maturation of mrine B lymphocyte precursors. *Mol. Immunol.*, 25:1113.

Gurunathan S, K. D. (2000). DNA vaccines: immunology, application, and optimization. *Ann. Rev. Immunol.* 2000, 18:927-974.

Haas, K. M. (2004). 3d functions as a molecular adjuvant in the absence of CD21/35 expression. *J. Immunol.*, 172: 5833.

Harms J S, O. S. (1999). Regulation of transgene expression in genetic immunization. *Braz. J. Med. Biol. Res*, 32:155-162.

Helen S Garmory, K. A. (2003). DNA vaccines: improving expression of antigens. *Genetic Vaccines and Therapy*, 1:2.

H L, D. (1997). Plasmid DNA expression systems for the purpose of immunization. *Curr. Opin. Biotechnol*, 8:635-640.

Hoffman S L, D. D. (1997). Strategy for development of a pre-erythrocytic *Plasmodium falciparum* DNA vaccine for human use. *Vaccine*, 15:842-5.

Irvine K R, R. J. (1996). Cytokine enhancement of DNA immunization leads to effective treatment of established pulmonary metastases. *J. Immunol.*, 156:238-45.

Itai K, S. D. (2001). Keratinocyte gene therapy: inducible promoters and in vivo control of transgene expression. *Clin Exp Dermatol*, 26:531-535.

Iwasaki A, S. B. (1997). Enhanced CTL responses mediated by plasmid DNA immunogens encoding costimulatory molecules and cytokines. *J. Immunol.*, 158:4591-601.

J J, K. (1999). Antigen-specific humoral and cellular immune response can be modulated in rhesus macaques through the use of IFN-gamma, IL-12, or IL-18 gene adjuvants. *J. Med. Primatol.*, 28:214-223.

JOHN D. LAMBRIS, V. S.-E. (1985). Mapping of the C3d receptor (CR2)-binding site and a neoantigenic site in the C3d domain of the third component of complement. *Proc. Natl. Acad. Sci. USA*, Vol. 82, pp. 4235-4239.

Kestler, H. I. (1991). Importance of the nef gene for maintenance of high virus loads and for development of AIDS. *Cell.*, 65:651-662.

Klinman, D. M. (1997). Contribution of CpG motifs to the immunogenicity of DNA vaccines. *J. Immunol.*, 158: 3635-3639.

Kuhrober A, W. J. (1997). DNA vaccination with plasmids encoding the intracellular (HBcAg) or secreted (HBeAg) form of the core protein of hepatitis B virus primes T cell responses to two overlapping Kb- and Kd-restricted epitopes. *Int Immunol.*, 9:1203-12.

Lachman, P. J. (1982). *J. Exp. Med.*, 156:205-216.

Lambris, J. (1980). *J. Exp. Med.*, 152:1625.

Leitner W W, S. M. (1997). Immune responses induced by intramuscular or gene gun injection of protective deoxyribonucleic acid vaccines that express the circumsporozoite protein from *Plasmodium berghei* malaria parasites. *J. Immunol.*, 159:6112-9.

Li X, S. S. (1998). Protection against respiratory syncytial virus infection by DNA immunization. *J Exp Med.*, 188: 681-8.

M, K. (1997). Recognition of AUG and alternative initiator codons is augmented by G in position +4 but is not generally affected by the nucleotides in positions +5 and +6. *EMBO J.*, 16:2482-2492.

Manickan E, K. K. (1997). DNA vaccines—a modern gimmick or a boon to vaccinology?. *Crit. Rev Immunol.*, 17:139-54.

M C, U. (1997). Cadherins and Langerhans cell immunobiology. *Clin Exp Immunol.*, 107:6-8.

Mellstedt H, F. J. (1999). Augmentation of the immune response with granulocyte-macrophage colony-stimulating factor and other hematopoietic growth factors. *Curr Opin Hematol.*, 6:169-75.

Merrifield, R. (1963). *J. Am. Chem. Soc.*, 85:2149-2154.

Migliorini, P. B. (1993). Malaria vaccine: immunization of mice with a synthetic T cell helper epitope alone leads to protective immunity. *Eur. J. Immunol.*, 23:582.

Minev B R, M. B. (1994). Insertion signal sequence fused to minimal peptides elicits specific CD8+ T-cell responses and prolongs survival of thymoma-bearing mice. *Cancer Res.*, 54:4155-61.

Montgomery D L, S. J. (1993). Heterologous and homologous protection against influenza A by DNA vaccination: optimization of DNA vectors. *DNA Cell Biol.*, 12:777-83.

Moran, P. a. (1994). Requirements for glycosylphosphatidylinositol attachment are similar but not identical in mammalian cells and parasitic protozoa. *J. Cell Biol.*, 125: 333-343.

N J, P. (1989). How RNA polymerase II terminates transcription in higher eukaryotes. *Trends Biochem. Sci,* 14:105-110.

Nussenzweig R. S., J. V. (1967). Protective immunity produced by the injection of X-irradiated sporozoites of *Plasmodium berghei. Nature,* Nature 216:160-162.

Nussenzweig, R. J. (1969). Protective immunity produced by the injection of X-irradiated sporozoites of *Plasmodium berghei*. IV. Dose response, specificity and humoral immunity. *Mil. Med.,* 134(Suppl.):1176-1182.

Nussenzweig. V., a. R. (1989). Rationale for the development of an engineered sporozoite malaria vaccine. *Adv. Immunol,* 45:283.

Pechhold K, P. N. (1997). Inflammatory cytokines IFN-gamma plus TNF-alpha induce regulated expression of CD80 (B7-1) but not CD86 (B7-2) on murine fibroblasts. *J. Immunol.,* 158:4921-9.

Potocnjak, P. N. (1980). Monovalent fragments (Fab) of monoclonal antibodies to a sporozoite surface antigen (Pb44) protect mice against malarial infection. *J. Exp. Med.,* 151:1504.

Prayaga S K, F. M. (1997). Manipulation of HIV-1 gp120-specific immune responses elicited via gene gun-based DNA immunization. *Vaccine,* 15:1349-52.

Restifo N, R. S. (1999). The development of recombinant and synthetic cancer vaccines. *Curr Opin Oncol.,* 11:50-7.

Rolls M M, W. P. (1994). Novel infectious particles generated by expression of the vesicular stomatitis virus glycoprotein from a self-replicating RNA. *Cell.,* 79:497-506.

Romero, P. J. (1990). Isolation and characterization of protective cytolytic T cells in a rodent malaria model system. *Immunol. Lett.,* 25:27.

Ross T M, X. Y. (2000). C3d enhancement of antibodies to hemagglutinin accelerates protection against influenza virus challenge. *Nature Immunol.,* 1:127-131.

Ross, G. a. (1985). Membrane complement receptors specific for bound fragments of C3. *Adv. Immunol.,* 37:217.

Ross, G. R. (1973). *J. Exp. Med.,* 138:798-811.

Sandra Scheiblhofer, D. C. (2001). Removal of the circumsporozoite protein (CSP) glycosylphosphatidylinositol signal sequence from a CSP DNA vaccine enhances induction of CSP-specific Th2 type immune responses and improves protection against malaria infection. *Eur. J. Immunol.,* 31: 692-698.

Sasaki S, T. T. (1997). Monophosphoryl lipid A enhances both humoral and cell-mediated immune responses to DNA vaccination against human immunodeficiency virus type 1. *Infect. Immun.,* 65:3520-8.

Scheiblhofer, S. C. (2001). Removal of the circumsporozoite protein (CSP) glycosylphosphatidylinositol signal sequence from a CSP DNA vaccine enhances induction of CSP-specific Th2 type immune responses and improves protection against malaria infection. *Eur. J. Immunol.,* 31:692.

Schirmbeck R, B. W. (1996). DNA vaccination primes MHC class I-restricted, simian virus 40 large tumor antigen-specific CTL in H-2d mice that reject syngeneic tumors. *J Immunol,* 157:3550-8.

Sedegah M, J. T. (1998). Boosting with recombinant vaccinia increases immunogenicity and protective efficacy of malaria DNA vaccine. *Proc Natl Acad Sci USA.,* 95:7648-53.

Servic, C. a. (1989). C3 synthetic peptides support growth of human CR2-positive lymphoblastoid cells. *J. Immunol.,* 142:2207.

Spier, R. (1996). International meeting on the nucleic acid vaccines for the prevention of infectious disease and regulating nucleic acid (DNA) vaccines. *Vaccine,* pp. 1285-8.

Steward, J., (1976). in *Peptides,* pp. 285-290.

Tamerius, J. P. (1985). *J. Immunol.*

Tsokos, G. C. (1990). Monovalent ligands of complement receptor 2 inhibit whereas polyvalent ligands enhance anti-Ig-induced human B cell intracytoplasmic free calcium concentration. *J. Immunol.,* 144:1640.

Tubulekas I, B. P. (1997). Alphavirus expression vectors and their use as recombinant vaccines: a minireview. *Gene,* 190:191-5.

Wang B, D. K. (1997). Mucosal immunization with a DNA vaccine induces immune responses against HIV-1 at a mucosal site. *Vaccine,* 15:821-5.

Weiner G J, L. H. (1997). Immunostimulatory oligodeoxynucleotides containing the CpG motif are effective as immune adjuvants in tumor antigen immunization. *Proc Natl Acad Sci USA.,* 94:10833-7.

Weis, J. T. (1984). Identification of a 145,000 Mr membrane protein as the C3d receptor (CR2) of human B lymphocytes. *Proc. Natl. Acad. Sci. USA,* Vol. 81, pp. 881-885.

Weiss, R. L. (2000). Genetic vaccination against malaria infection by intradermal and epidermal injections of a plasmid containing the gene encoding the *Plasmodium berghei* circumsporozoite protein. *Infect. Immun.,* 68:5914.

Williams R S, J. S. (1991). Introduction of foreign genes into tissues of living mice by DNA-coated microprojectiles. *Proc Natl Acad Sci USA.,* 88:2726-30.

Wolff J A, M. R. (1990). Direct gene transfer into mouse muscle in vivo. *Science,* 247:1465-8.

Wolfgang W. Leitner, *. M. (1997). Immune Responses Induced by Intramuscular or Gene Gun Injection of Protective Deoxyribonucleic Acid Vaccines That Express the Circumsporozoite Protein from *Plasmodium berghei* Malaria Parasites. *Journal of Immunology,* 159:6112-6119.

Wolfgang W. Leitner, H. Y. (1999). DNA and RNA-based vaccines: principles, progress and prospects. *Vaccine,* 18(9-10): 765-777.

Wright, S. D. (1983). *Proc. Natl. Acad. Sci. USA,* 80:5699-5703.

Xu Z-L, M. H.-W. (2001). Optimization of transcriptional regulatory elements for constructing plasmid vectors. *Gene,* 272:149-156.

Zavala, F. A. (1983). *Circumsporozoite protein of malaria parasites contains a single immunodominant region with two or more identical epitopes.,* J. Exp. Med. 157:1947-1957.

Zavala, F. A. (1983). Circumsporozoite protein of malaria parasites contains a single immunodominant region with two or more identical epitopes. *J. Exp. Med.,* 157:1947-1957.

What is claimed is:

1. An isolated nucleic acid encoding a fusion protein comprising Plasmodium circumsporozoite protein (CSP) and at least one p28 molecule from the croup consisting of SEQ. ID. NO. 25 and SEQ. ID. NO 26, wherein the CSP is SEQ. ID. NO. 28 or SEQ. ID. NO 35.

2. An expression vector comprising the nucleic acid according to claim 1 and further comprising regulatory sequences for expression of the fusion protein.

3. A host murine cell comprising the vector according to claim 2.

4. A composition comprising the vector according to claim 2 and a pharmaceutically acceptable excipient or carrier.

5. A method of constructing a nucleic acid encoding a fusion protein comprising a peptide or polypeptide antigen and more than one human (SEQ. ID. NO. 25) or murine (SEQ. ID. NO. 26) p28 molecule comprising the steps of:
   constructing a full length Plasmodium CSP without the GPI-anchor sequence CSP(–A) (SEQ. ID. NO. 28);
   amplifying the C-terminal part of CSP (SEQ. ID. NO. 28) from pCI-CSP-3xC3d using OAN443 (SEQ. ID. NO. 29) and OAN444 (SEQ. ID. NO. 30) yield a first PCR product;
   enzymatically lysing the first PCR product yielding a first enzymatic product;
   ligating the first enzymatic product into a first clone;
   amplifying the p28 fragment of C3d from pCI-CSP-3xC3d using OAN445 (SEQ. ID. NO. 15) and OAN446 (SEQ ID. NO. 16) yielding a second PCR product;
   enzymatically lysing the second PCR product yielding a second enzymatic product;
   ligating said second enzymatic product into the first clone, in combination with a linker, yielding a second clone;
   enzymatically lysing the second clone yielding a third enzymatic product;
   ligating the second enzymatic product into the third enzymatic product, in combination with a linker, yielding a third clone;
   enzymatically lysing the third clone yielding a fourth enzymatic product;
   ligating the second enzymatic product into the fourth enzymatic product, in combination with a linker, yielding a fourth clone;
   enzymatically lysing pCI-CSP-3xC3d yielding a fifth enzymatic product;
   enzymatically lysing the fourth clone yielding a sixth enzymatic product; and,
   ligating the fifth enzymatic product into the sixth enzymatic product, in combination with a linker, yielding a fifth clone.

6. The method of claim 5 wherein the enzymatic lysing is accomplished with an enzymatic restrictase selected from a group consisting of: BGIII/EcoRI, XbaI/EcoRI, BamHI/EcoRI, and Afl HH/EcoRI.

7. The method of claim 5 wherein the antigen is CSP (SEQ. ID. NO. 28).

8. The method of claim 5 wherein the p28 fragment is coupled to the antigen via a peptide bond.

9. The method of claim 5 wherein the p28 fragment is coupled to the antigen via a chemical bond.

10. A method of claim 5 wherein the conjugate molecule is made by expression from encoding nucleic acid.

* * * * *

SEQUENCE LISTING

```
<160> NUMBER OF SEQ ID NOS: 36

<210> SEQ ID NO 1
<211> LENGTH: 27
<212> TYPE: DNA
<213> ORGANISM: Artificial
<220> FEATURE:
<223> OTHER INFORMATION: The forward primer of a murine C3d DNA fragment

<400> SEQUENCE: 1
gggagatcta cccccgcagg ctctggg                                    27

<210> SEQ ID NO 2
<211> LENGTH: 30
<212> TYPE: DNA
<213> ORGANISM: Artificial
<220> FEATURE:
<223> OTHER INFORMATION: The reverse primer of a murine C3d DNA
      fragment.

<400> SEQUENCE: 2
ggggatccgg ggaggtggaa ggacacatcc                                 30

<210> SEQ ID NO 3
<211> LENGTH: 48
<212> TYPE: DNA
<213> ORGANISM: Artificial
<220> FEATURE:
<223> OTHER INFORMATION: Linker oligonucleotides used in creating pCI-
      TPA/2C3n plasmid

<400> SEQUENCE: 3
gatctggagg aggaggctcc ggaggaggag gctccggatc cgaattca             48

<210> SEQ ID NO 4
<211> LENGTH: 48
<212> TYPE: DNA
<213> ORGANISM: Artificial
<220> FEATURE:
<223> OTHER INFORMATION: Linker oligonucleotides used in constructing
      pCI-TPA/2C3n plasmid

<400> SEQUENCE: 4
agcttgaatt cggatccgga gcctcctcct ccggagcctc ctcctcca             48

<210> SEQ ID NO 5
<211> LENGTH: 19
<212> TYPE: DNA
<213> ORGANISM: Artificial
<220> FEATURE:
<223> OTHER INFORMATION: Forward primer for PCR of CSP N-T 1311

<400> SEQUENCE: 5
gtcagcggat ccgatggac                                             19

<210> SEQ ID NO 6
<211> LENGTH: 39
<212> TYPE: DNA
<213> ORGANISM: Artificial
<220> FEATURE:
<223> OTHER INFORMATION: Reverse primer of CSP N-T 1370

<400> SEQUENCE: 6
tggtggtggg gatccttgtt tcaatttatt attacgctc                       39
```

```
<210> SEQ ID NO 7
<211> LENGTH: 53
<212> TYPE: DNA
<213> ORGANISM: Artificial
<220> FEATURE:
<223> OTHER INFORMATION: Forward primer for PCR of CSP C-T 1809

<400> SEQUENCE: 7
caaccaggat ccggtggtaa taacaataac aaaaataata ataatgacga ttc          53

<210> SEQ ID NO 8
<211> LENGTH: 20
<212> TYPE: DNA
<213> ORGANISM: Artificial
<220> FEATURE:
<223> OTHER INFORMATION: Reverse PCR primer for CSP C-T 2072

<400> SEQUENCE: 8
tcttcaggat ccacttgaac                                               20

<210> SEQ ID NO 9
<211> LENGTH: 15
<212> TYPE: DNA
<213> ORGANISM: Artificial
<220> FEATURE:
<223> OTHER INFORMATION: Stop, sense cloning oligonucleotides used in
      constructing pCI-TPA, stop, -EEF motif

<400> SEQUENCE: 9
ctagcggatc ctgaa                                                    15

<210> SEQ ID NO 10
<211> LENGTH: 15
<212> TYPE: DNA
<213> ORGANISM: Artificial
<220> FEATURE:
<223> OTHER INFORMATION: Stop, nonsense oligonucleotides used in
      constructing pCI-TPA, stop, -EEF motif

<400> SEQUENCE: 10
gatcttcagg atccg                                                    15

<210> SEQ ID NO 11
<211> LENGTH: 21
<212> TYPE: DNA
<213> ORGANISM: Artificial
<220> FEATURE:
<223> OTHER INFORMATION: Adapter, sense oligonucleotide used in
      constructing CSP +A plasmid

<400> SEQUENCE: 11
ttaggatccg aggaattctg a                                             21

<210> SEQ ID NO 12
<211> LENGTH: 27
<212> TYPE: DNA
<213> ORGANISM: Artificial
<220> FEATURE:
<223> OTHER INFORMATION: Adapter, nonsense oligonucleotides used in
      constructing CSP +A plasmid

<400> SEQUENCE: 12
gatctcagaa ttcctcggat cctaaat                                       27

<210> SEQ ID NO 13
<211> LENGTH: 20
<212> TYPE: DNA
<213> ORGANISM: Artificial
```

```
<220> FEATURE:
<223> OTHER INFORMATION: PCR, sense oligonucleotide used to replicate
      pCI-TPA(PbCSP6618) plasmid

<400> SEQUENCE: 13
gctagcacat gtggttctgg                                                   20

<210> SEQ ID NO 14
<211> LENGTH: 37
<212> TYPE: DNA
<213> ORGANISM: Artificial
<220> FEATURE:
<223> OTHER INFORMATION: PCR, nonsense oligonucleotide used to replicate
      pCI-TPA(PbCSP6618) plasmid

<400> SEQUENCE: 14
ttacctattt acaagttcac cttaaggagt ctagaat                                37

<210> SEQ ID NO 15
<211> LENGTH: 65
<212> TYPE: DNA
<213> ORGANISM: Artificial
<220> FEATURE:
<223> OTHER INFORMATION: primer for p28 fragment of C3d from pCI-CSP-
      3xC3d construct

<400> SEQUENCE: 15
aatgcacaga tctggaggcg gcggttcagg aggcggcggt agcaagtttc tgaacacagc       60
caaag                                                                   65

<210> SEQ ID NO 16
<211> LENGTH: 40
<212> TYPE: DNA
<213> ORGANISM: Artificial
<220> FEATURE:
<223> OTHER INFORMATION: primer for p28 fragment of C3d from pCI-CSP-
      3xC3d construct

<400> SEQUENCE: 16
aatgcgaatt cttaggatcc ggcgtaggat gtggcctcta                             40

<210> SEQ ID NO 17
<211> LENGTH: 11
<212> TYPE: DNA
<213> ORGANISM: Artificial
<220> FEATURE:
<223> OTHER INFORMATION: Linker oligonucleotides used to consruct
      WRG-6518 vector

<400> SEQUENCE: 17
cggatccgcc g                                                            11

<210> SEQ ID NO 18
<211> LENGTH: 69
<212> TYPE: DNA
<213> ORGANISM: Artificial
<220> FEATURE:
<223> OTHER INFORMATION: Synthetic mimic of the tissue plasminogen
      activator leader sequence

<400> SEQUENCE: 18
atggatgcaa tgaagagagg gctctgctgt gtgctgctgc tgtgtggagc agtcttcgtt       60
tcggctagc                                                               69

<210> SEQ ID NO 19
<211> LENGTH: 43
```

```
<212> TYPE: DNA
<213> ORGANISM: Artificial
<220> FEATURE:
<223> OTHER INFORMATION: japcr19 primer

<400> SEQUENCE: 19
gtcgctccaa gcttgctagc caatatgtca cagtcttta tgg                    43

<210> SEQ ID NO 20
<211> LENGTH: 51
<212> TYPE: DNA
<213> ORGANISM: Artificial
<220> FEATURE:
<223> OTHER INFORMATION: 3' primer for sgp110 (hkpcr2)

<400> SEQUENCE: 20
cccgggatcc tatgcgggcg ccaggccaat cggagtgatc tctactaatt t          51

<210> SEQ ID NO 21
<211> LENGTH: 37
<212> TYPE: DNA
<213> ORGANISM: Artificial
<220> FEATURE:
<223> OTHER INFORMATION: 3' primer for sgp130 (jw8)

<400> SEQUENCE: 21
cgggatccta tgcgggcgcc aggtcaaacc aattgcc                          37

<210> SEQ ID NO 22
<211> LENGTH: 24
<212> TYPE: DNA
<213> ORGANISM: Artificial
<220> FEATURE:
<223> OTHER INFORMATION: PCR 5' primer to amplify hTPA/CSP insert in
      WRG-6518

<400> SEQUENCE: 22
gggctcgaga tggatgcaat gaag                                        24

<210> SEQ ID NO 23
<211> LENGTH: 36
<212> TYPE: DNA
<213> ORGANISM: Artificial
<220> FEATURE:
<223> OTHER INFORMATION: Antisense PCR primer to amplify the hTPA/SCP
      insert in WRG-6518

<400> SEQUENCE: 23
cccgcggccg cttaattaaa gaatactaat actaat                           36

<210> SEQ ID NO 24
<211> LENGTH: 24
<212> TYPE: PRT
<213> ORGANISM: Plasmodium berghei

<400> SEQUENCE: 24

Asp Pro Pro Pro Pro Asn Pro Asn Asp Pro Pro Pro Pro Asn Pro Asn
1               5                   10                  15

Asp Pro Pro Pro Pro Asn Pro Asn
            20

<210> SEQ ID NO 25
<211> LENGTH: 28
<212> TYPE: PRT
<213> ORGANISM: Homo sapiens

<400> SEQUENCE: 25
```

Lys Phe Leu Thr Thr Ala Lys Asp Lys Asn Arg Trp Glu Asp Pro Gly
1               5                   10                  15

Lys Gln Leu Tyr Asn Val Glu Ala Thr Ser Tyr Ala
            20                  25

<210> SEQ ID NO 26
<211> LENGTH: 84
<212> TYPE: DNA
<213> ORGANISM: Mus musculus

<400> SEQUENCE: 26
aagtttctga acacagccaa agatcggaac cgctgggagg agcctgacca gcagctctac    60
aacgtagagg ccacatccta cgcc    84

<210> SEQ ID NO 27
<211> LENGTH: 1662
<212> TYPE: PRT
<213> ORGANISM: Mus musculus

<400> SEQUENCE: 27

Met Gly Pro Ala Ser Gly Ser Gln Leu Leu Val Leu Leu Leu Leu Leu
1               5                   10                  15

Ala Ser Ser Pro Leu Ala Leu Gly Ile Pro Met Tyr Ser Ile Ile Thr
            20                  25                  30

Pro Asn Val Leu Arg Leu Glu Ser Glu Glu Thr Ile Val Leu Glu Ala
        35                  40                  45

His Asp Ala Gln Gly Asp Ile Pro Val Thr Val Thr Val Gln Asp Phe
    50                  55                  60

Leu Lys Arg Gln Val Leu Ser Glu Lys Thr Val Leu Thr Gly Ala Ser
65                  70                  75                  80

Gly His Leu Arg Ser Val Ser Ile Lys Ile Pro Ala Ser Lys Glu Phe
                85                  90                  95

Asn Ser Asp Lys Glu Gly His Lys Tyr Val Thr Val Val Ala Asn Phe
            100                 105                 110

Gly Glu Thr Val Val Glu Lys Ala Val Met Val Ser Phe Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asp Asn Asn Leu Leu Pro Val Gly
145                 150                 155                 160

Lys Thr Val Val Ile Leu Ile Glu Thr Pro Asp Gly Ile Pro Val Lys
                165                 170                 175

Arg Asp Ile Leu Ser Ser Asn Asn Gln His Gly Ile Leu Pro Leu Ser
            180                 185                 190

Trp Asn Ile Pro Glu Leu Val Asn Met Gly Gln Trp Lys Ile Arg Ala
        195                 200                 205

Phe Tyr Glu His Ala Pro Lys Gln Ile Phe Ser Ala Glu Phe Glu Val
    210                 215                 220

Lys Glu Tyr Val Leu Pro Ser Phe Glu Val Arg Val Glu Pro Thr Glu
225                 230                 235                 240

Thr Phe Tyr Tyr Ile Asp Asp Pro Asn Gly Leu Glu Val Ser Ile Ile
                245                 250                 255

Ala Lys Phe Leu Tyr Gly Lys Asn Val Asp Gly Thr Ala Phe Val Ile
            260                 265                 270

Phe Gly Val Gln Asp Gly Asp Lys Lys Ile Ser Leu Ala His Ser Leu
        275                 280                 285

```
Thr Arg Val Val Ile Glu Asp Gly Val Gly Asp Ala Val Leu Thr Arg
    290                 295                 300
Lys Val Leu Met Glu Gly Val Arg Pro Ser Asn Ala Asp Ala Leu Val
305                 310                 315                 320
Gly Lys Ser Leu Tyr Val Ser Val Thr Val Ile Leu His Ser Gly Ser
                325                 330                 335
Asp Met Val Glu Ala Glu Arg Ser Gly Ile Pro Ile Val Thr Ser Pro
            340                 345                 350
Tyr Gln Ile His Phe Thr Lys Thr Pro Lys Phe Phe Lys Pro Ala Met
        355                 360                 365
Pro Phe Asp Leu Met Val Phe Val Thr Asn Pro Asp Gly Ser Pro Ala
370                 375                 380
Ser Lys Val Leu Val Val Thr Gln Gly Ser Asn Ala Lys Ala Leu Thr
385                 390                 395                 400
Gln Asp Asp Gly Val Ala Lys Leu Ser Ile Asn Thr Pro Asn Ser Arg
                405                 410                 415
Gln Pro Leu Thr Ile Thr Val Arg Thr Lys Lys Asp Thr Leu Pro Glu
            420                 425                 430
Ser Arg Gln Ala Thr Lys Thr Met Glu Ala His Pro Tyr Ser Thr Met
        435                 440                 445
His Asn Ser Asn Asn Tyr Leu His Leu Ser Val Ser Arg Met Glu Leu
450                 455                 460
Lys Pro Gly Asp Asn Leu Asn Val Asn Phe His Leu Arg Thr Asp Pro
465                 470                 475                 480
Gly His Glu Ala Lys Ile Arg Tyr Tyr Thr Tyr Leu Val Met Asn Lys
                485                 490                 495
Gly Lys Leu Leu Lys Ala Gly Arg Gln Val Arg Glu Pro Gly Gln Asp
            500                 505                 510
Leu Val Val Leu Ser Leu Pro Ile Thr Pro Glu Phe Ile Pro Ser Phe
        515                 520                 525
Arg Leu Val Ala Tyr Tyr Thr Leu Ile Gly Ala Ser Gly Gln Arg Glu
530                 535                 540
Val Val Ala Asp Ser Val Trp Val Asp Val Lys Asp Ser Cys Ile Gly
545                 550                 555                 560
Thr Leu Val Val Lys Gly Asp Pro Arg Asp Asn His Leu Ala Pro Gly
                565                 570                 575
Gln Gln Thr Thr Leu Arg Ile Glu Gly Asn Gln Gly Ala Arg Val Gly
            580                 585                 590
Leu Val Ala Val Asp Lys Gly Val Phe Val Leu Asn Lys Lys Asn Lys
        595                 600                 605
Leu Thr Gln Ser Lys Ile Trp Asp Val Val Glu Lys Ala Asp Ile Gly
610                 615                 620
Cys Thr Pro Gly Ser Gly Lys Asn Tyr Ala Gly Val Phe Met Asp Ala
625                 630                 635                 640
Gly Leu Ala Phe Lys Thr Ser Gln Gly Leu Gln Thr Glu Gln Arg Ala
                645                 650                 655
Asp Leu Glu Cys Thr Lys Pro Ala Ala Arg Arg Arg Arg Ser Val Gln
            660                 665                 670
Leu Met Glu Arg Arg Met Asp Lys Ala Gly Gln Tyr Thr Asp Lys Gly
        675                 680                 685
Leu Arg Lys Cys Cys Glu Asp Gly Met Arg Asp Ile Pro Met Arg Tyr
690                 695                 700
Ser Cys Gln Arg Arg Ala Arg Leu Ile Thr Gln Gly Glu Asn Cys Ile
```

```
            705                 710                 715                 720
Lys Ala Phe Ile Asp Cys Cys Asn His Ile Thr Lys Leu Arg Glu Gln
                    725                 730                 735

His Arg Arg Asp His Val Leu Gly Leu Ala Arg Ser Glu Leu Glu Glu
                    740                 745                 750

Asp Ile Ile Pro Glu Glu Asp Ile Ile Ser Arg Ser His Phe Pro Gln
                    755                 760                 765

Ser Trp Leu Trp Thr Ile Glu Glu Leu Lys Pro Glu Lys Asn Gly
                    770                 775             780

Ile Ser Thr Lys Val Met Asn Ile Phe Leu Lys Asp Ser Ile Thr Thr
785                 790                 795                 800

Trp Glu Ile Leu Ala Val Ser Leu Ser Asp Lys Lys Gly Ile Cys Val
                    805                 810                 815

Ala Asp Pro Tyr Glu Ile Arg Val Met Gln Asp Phe Phe Ile Asp Leu
                    820                 825                 830

Arg Leu Pro Tyr Ser Val Arg Asn Glu Gln Val Glu Ile Arg Ala
                    835                 840                 845

Val Leu Phe Asn Tyr Arg Glu Gln Glu Glu Leu Lys Val Arg Val Glu
850                 855                 860

Leu Leu His Asn Pro Ala Phe Cys Ser Met Ala Thr Ala Lys Asn Arg
865                 870                 875                 880

Tyr Phe Gln Thr Ile Lys Ile Pro Pro Lys Ser Ser Val Ala Val Pro
                    885                 890                 895

Tyr Val Ile Val Pro Leu Lys Ile Gly Gln Gln Glu Val Glu Val Lys
                    900                 905                 910

Ala Ala Val Phe Asn His Phe Ile Ser Asp Gly Val Lys Lys Thr Leu
                    915                 920                 925

Lys Val Val Pro Glu Gly Met Arg Ile Asn Lys Thr Val Ala Ile His
930                 935                 940

Thr Leu Asp Pro Glu Lys Leu Gly Gln Gly Gly Val Gln Lys Val Asp
945                 950                 955                 960

Val Pro Ala Ala Asp Leu Ser Asp Gln Val Pro Asp Thr Asp Ser Glu
                    965                 970                 975

Thr Arg Ile Ile Leu Gln Gly Ser Pro Val Val Gln Met Ala Glu Asp
                    980                 985                 990

Ala Val Asp Gly Glu Arg Leu Lys His Leu Ile Val Thr Pro Ala Gly
                    995                 1000                1005

Cys Gly Glu Gln Asn Met Ile Gly Met Thr Pro Thr Val Ile Ala
                    1010                1015                1020

Val His Tyr Leu Asp Gln Thr Glu Gln Trp Glu Lys Phe Gly Ile
                    1025                1030                1035

Glu Lys Arg Gln Glu Ala Leu Glu Leu Ile Lys Lys Gly Tyr Thr
                    1040                1045                1050

Gln Gln Leu Ala Phe Lys Gln Pro Ser Ser Ala Tyr Ala Ala Phe
                    1055                1060                1065

Asn Asn Arg Pro Pro Ser Thr Trp Leu Thr Ala Tyr Val Val Lys
                    1070                1075                1080

Val Phe Ser Leu Ala Ala Asn Leu Ile Ala Ile Asp Ser His Val
                    1085                1090                1095

Leu Cys Gly Ala Val Lys Trp Leu Ile Leu Glu Lys Gln Lys Pro
                    1100                1105                1110

Asp Gly Val Phe Gln Glu Asp Gly Pro Val Ile His Gln Glu Met
                    1115                1120                1125
```

-continued

Ile Gly Gly Phe Arg Asn Ala Lys Glu Ala Asp Val Ser Leu Thr
1130                1135                1140

Ala Phe Val Leu Ile Ala Leu Gln Glu Ala Arg Asp Ile Cys Glu
1145                1150                1155

Gly Gln Val Asn Ser Leu Pro Gly Ser Ile Asn Lys Ala Gly Glu
1160                1165                1170

Tyr Ile Glu Ala Ser Tyr Met Asn Leu Gln Arg Pro Tyr Thr Val
1175                1180                1185

Ala Ile Ala Gly Tyr Ala Leu Ala Leu Met Asn Lys Leu Glu Glu
1190                1195                1200

Pro Tyr Leu Gly Lys Phe Leu Asn Thr Ala Lys Asp Arg Asn Arg
1205                1210                1215

Trp Glu Glu Pro Asp Gln Gln Leu Tyr Asn Val Glu Ala Thr Ser
1220                1225                1230

Tyr Ala Leu Leu Ala Leu Leu Leu Lys Asp Phe Asp Ser Val
1235                1240                1245

Pro Pro Val Val Arg Trp Leu Asn Glu Gln Arg Tyr Tyr Gly Gly
1250                1255                1260

Gly Tyr Gly Ser Thr Gln Ala Thr Phe Met Val Phe Gln Ala Leu
1265                1270                1275

Ala Gln Tyr Gln Thr Asp Val Pro Asp His Lys Asp Leu Asn Met
1280                1285                1290

Asp Val Ser Phe His Leu Pro Ser Arg Ser Ser Ala Thr Thr Phe
1295                1300                1305

Arg Leu Leu Trp Glu Asn Gly Asn Leu Leu Arg Ser Glu Glu Thr
1310                1315                1320

Lys Gln Asn Glu Ala Phe Ser Leu Thr Ala Lys Gly Lys Gly Arg
1325                1330                1335

Gly Thr Leu Ser Val Val Ala Val Tyr His Ala Lys Leu Lys Ser
1340                1345                1350

Lys Val Thr Cys Lys Lys Phe Asp Leu Arg Val Ser Ile Arg Pro
1355                1360                1365

Ala Pro Glu Thr Ala Lys Lys Pro Glu Glu Ala Lys Asn Thr Met
1370                1375                1380

Phe Leu Glu Ile Cys Thr Lys Tyr Leu Gly Asp Val Asp Ala Thr
1385                1390                1395

Met Ser Ile Leu Asp Ile Ser Met Met Thr Gly Phe Ala Pro Asp
1400                1405                1410

Thr Lys Asp Leu Glu Leu Leu Ala Ser Gly Val Asp Arg Tyr Ile
1415                1420                1425

Ser Lys Tyr Glu Met Asn Lys Ala Phe Ser Asn Lys Asn Thr Leu
1430                1435                1440

Ile Ile Tyr Leu Glu Lys Ile Ser His Thr Glu Glu Asp Cys Leu
1445                1450                1455

Thr Phe Lys Val His Gln Tyr Phe Asn Val Gly Leu Ile Gln Pro
1460                1465                1470

Gly Ser Val Lys Val Tyr Ser Tyr Tyr Asn Leu Glu Glu Ser Cys
1475                1480                1485

Thr Arg Phe Tyr His Pro Glu Lys Asp Asp Gly Met Leu Ser Lys
1490                1495                1500

Leu Cys His Ser Glu Met Cys Arg Cys Ala Glu Glu Asn Cys Phe
1505                1510                1515

Met Gln Gln Ser Gln Glu Lys Ile Asn Leu Asn Val Arg Leu Asp
1520                1525                1530

-continued

Lys Ala Cys Glu Pro Gly Val Asp Tyr Val Tyr Lys Thr Glu Leu
1535                1540                1545

Thr Asn Ile Glu Leu Leu Asp Asp Phe Asp Glu Tyr Thr Met Thr
    1550                1555                1560

Ile Gln Gln Val Ile Lys Ser Gly Ser Asp Glu Val Gln Ala Gly
1565                1570                1575

Gln Gln Arg Lys Phe Ile Ser His Ile Lys Cys Arg Asn Ala Leu
1580                1585                1590

Lys Leu Gln Lys Gly Lys Lys Tyr Leu Met Trp Gly Leu Ser Ser
1595                1600                1605

Asp Leu Trp Gly Glu Lys Pro Asn Thr Ser Tyr Ile Ile Gly Lys
1610                1615                1620

Asp Thr Trp Val Glu His Trp Pro Glu Ala Glu Cys Gln Asp
1625                1630                1635

Gln Lys Tyr Gln Lys Gln Cys Glu Glu Leu Gly Ala Phe Thr Glu
1640                1645                1650

Ser Met Val Val Tyr Gly Cys Pro Asn
1655                1660

<210> SEQ ID NO 28
<211> LENGTH: 305
<212> TYPE: PRT
<213> ORGANISM: Mus musculus

<400> SEQUENCE: 28

Ala Gln Arg Asn Leu Asn Glu Leu Cys Tyr Asn Glu Gly Asn Asp Asn
1               5                   10                  15

Lys Leu Tyr His Val Leu Asn Ser Lys Asn Gly Lys Ile Tyr Asn Arg
            20                  25                  30

Asn Thr Val Asn Arg Leu Leu Pro Met Leu Arg Arg Lys Lys Asn Glu
        35                  40                  45

Lys Lys Asn Glu Lys Ile Glu Arg Asn Asn Lys Leu Lys Gln Pro Pro
50                  55                  60

Pro Pro Pro Asn Pro Asn Asp Pro Pro Pro Asn Pro Asn Asp Pro
65                  70                  75                  80

Pro Pro Pro Asn Pro Asn Asp Pro Pro Pro Asn Pro Asn Asp Pro
            85                  90                  95

Pro Pro Pro Asn Ala Asn Asp Pro Pro Pro Asn Ala Asn Asp Pro
        100                 105                 110

Ala Pro Pro Asn Ala Asn Asp Pro Ala Pro Pro Asn Ala Asn Asp Pro
            115                 120                 125

Ala Pro Pro Asn Ala Asn Asp Pro Ala Pro Pro Asn Ala Asn Asp Pro
130                 135                 140

Ala Pro Pro Asn Ala Asn Asp Pro Ala Pro Pro Asn Ala Asn Asp Pro
145                 150                 155                 160

Pro Pro Pro Asn Pro Asn Asp Pro Ala Pro Pro Gln Gly Asn Asn Asn
                165                 170                 175

Pro Gln Pro Gln Pro Arg Pro Gln Pro Gln Gln Pro Gln Pro Gln
            180                 185                 190

Pro Gln Pro Gln Pro Gln Pro Gln Pro Arg Pro Gln Pro Gln Pro Gln
        195                 200                 205

Pro Gly Gly Asn Asn Asn Asn Lys Asn Asn Asn Asn Asp Asp Ser Tyr
            210                 215                 220

Ile Pro Ser Ala Glu Lys Ile Leu Glu Phe Val Lys Gln Ile Arg Asp
225                 230                 235                 240

```
Ser Ile Thr Glu Glu Trp Ser Gln Cys Asn Val Thr Cys Gly Ser Gly
            245                 250                 255

Ile Arg Val Arg Lys Arg Lys Gly Ser Asn Lys Lys Ala Glu Asp Leu
                260                 265                 270

Thr Leu Glu Asp Ile Asp Thr Glu Ile Cys Lys Met Asp Lys Cys Ser
            275                 280                 285

Ser Ile Phe Asn Ile Val Ser Asn Ser Leu Gly Phe Val Ile Leu Leu
        290                 295                 300

Val
305

<210> SEQ ID NO 29
<211> LENGTH: 33
<212> TYPE: DNA
<213> ORGANISM: Artificial
<220> FEATURE:
<223> OTHER INFORMATION: primer for C-terminal part of CSP of pCI-CSP-
      3xC3d construct

<400> SEQUENCE: 29
aatgctctag aacatgtggt tctggtataa gag                              33

<210> SEQ ID NO 30
<211> LENGTH: 46
<212> TYPE: DNA
<213> ORGANISM: Artificial
<220> FEATURE:
<223> OTHER INFORMATION: primer for C-terminal part of CSP of pCI-CSP-
      3xC3d construct

<400> SEQUENCE: 30
aatgcgaatt cttaggatcc acttgaacat ttatccattt tacaaa                46

<210> SEQ ID NO 31
<211> LENGTH: 28
<212> TYPE: DNA
<213> ORGANISM: Artificial
<220> FEATURE:
<223> OTHER INFORMATION: Linker DNA in construct pCSD-linker-p28-
      linker-p28-linker-p28

<400> SEQUENCE: 31
aggcggcggt tcaggaggcg gcggtagc                                    28

<210> SEQ ID NO 32
<211> LENGTH: 10
<212> TYPE: PRT
<213> ORGANISM: Artificial
<220> FEATURE:
<223> OTHER INFORMATION: Linker AA in construct pAN494
      (CSP-G4SG4S-p28-G4SG4S-p28-G4SG4S-p28-STOP)

<400> SEQUENCE: 32

Gly Gly Gly Gly Ser Gly Gly Gly Gly Ser
1               5                   10

<210> SEQ ID NO 33
<211> LENGTH: 1663
<212> TYPE: PRT
<213> ORGANISM: Homo sapiens

<400> SEQUENCE: 33

Met Gly Pro Thr Ser Gly Pro Ser Leu Leu Leu Leu Leu Leu Thr His
1               5                   10                  15
```

-continued

```
Leu Pro Leu Ala Leu Gly Ser Pro Met Tyr Ser Ile Ile Thr Pro Asn
         20                  25                  30

Ile Leu Arg Leu Glu Ser Glu Thr Met Val Leu Glu Ala His Asp
         35                  40                  45

Ala Gln Gly Asp Val Pro Val Thr Val Thr Val His Asp Phe Pro Gly
 50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Ala Thr Phe
            100                 105                 110

Gly Thr Gln Val Val Glu Lys Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
        195                 200                 205

Tyr Tyr Glu Asn Ser Pro Gln Gln Val Phe Ser Thr Glu Phe Glu Val
    210                 215                 220

Lys Glu Tyr Val Leu Pro Ser Phe Glu Val Ile Val Glu Pro Thr Glu
225                 230                 235                 240

Lys Phe Tyr Tyr Ile Tyr Asn Glu Lys Gly Leu Glu Val Thr Ile Thr
                245                 250                 255

Ala Arg Phe Leu Tyr Gly Lys Lys Val Glu Gly Thr Ala Phe Val Ile
            260                 265                 270

Phe Gly Ile Gln Asp Gly Glu Gln Arg Ile Ser Leu Pro Glu Ser Leu
        275                 280                 285

Lys Arg Ile Pro Ile Glu Asp Gly Ser Gly Glu Val Val Leu Ser Arg
    290                 295                 300

Lys Val Leu Leu Asp Gly Val Gln Asn Pro Arg Ala Glu Asp Leu Val
305                 310                 315                 320

Gly Lys Ser Leu Tyr Val Ser Ala Thr Val Ile Leu His Ser Gly Ser
                325                 330                 335

Asp Met Val Gln Ala Glu Arg Ser Gly Ile Pro Ile Val Thr Ser Pro
            340                 345                 350

Tyr Gln Ile His Phe Thr Lys Thr Pro Lys Tyr Phe Lys Pro Gly Met
        355                 360                 365

Pro Phe Asp Leu Met Val Phe Val Thr Asn Pro Asp Gly Ser Pro Ala
    370                 375                 380

Tyr Arg Val Pro Val Ala Val Gln Gly Glu Asp Thr Val Gln Ser Leu
385                 390                 395                 400

Thr Gln Gly Asp Gly Val Ala Lys Leu Ser Ile Asn Thr His Pro Ser
                405                 410                 415

Gln Lys Pro Leu Ser Ile Thr Val Arg Thr Lys Lys Gln Glu Leu Ser
            420                 425                 430

Glu Ala Glu Gln Ala Thr Arg Thr Met Gln Ala Leu Pro Tyr Ser Thr
        435                 440                 445
```

```
Val Gly Asn Ser Asn Asn Tyr Leu His Leu Ser Val Leu Arg Thr Glu
    450                 455                 460

Leu Arg Pro Gly Glu Thr Leu Asn Val Asn Phe Leu Leu Arg Met Asp
465                 470                 475                 480

Arg Ala His Glu Ala Lys Ile Arg Tyr Tyr Thr Tyr Leu Ile Met Asn
                485                 490                 495

Lys Gly Arg Leu Leu Lys Ala Gly Arg Gln Val Arg Glu Pro Gly Gln
                500                 505                 510

Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Ser Gly Gln Arg
        530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
                580                 585                 590

Val Val Leu Val Ala Val Asp Lys Gly Val Phe Val Leu Asn Lys Lys
            595                 600                 605

Asn Lys Leu Thr Gln Ser Lys Ile Trp Asp Val Val Glu Lys Ala Asp
        610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Ser Gly Gln Gln Thr Ala Gln
                645                 650                 655

Arg Ala Glu Leu Gln Cys Pro Gln Pro Ala Ala Arg Arg Arg Arg Ser
                660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
        690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
                740                 745                 750

Glu Asp Ile Ile Ala Glu Glu Asn Ile Val Ser Arg Ser Glu Phe Pro
            755                 760                 765

Glu Ser Trp Leu Trp Asn Val Glu Asp Leu Lys Glu Pro Pro Lys Asn
        770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
                820                 825                 830

Leu Arg Leu Pro Tyr Ser Val Val Arg Asn Glu Gln Val Glu Ile Arg
            835                 840                 845

Ala Val Leu Tyr Asn Tyr Arg Gln Asn Gln Glu Leu Lys Val Arg Val
        850                 855                 860

Glu Leu Leu His Asn Pro Ala Phe Cys Ser Leu Ala Thr Thr Lys Arg
```

-continued

```
        865              870              875              880
Arg His Gln Gln Thr Val Thr Ile Pro Pro Lys Ser Ser Leu Ser Val
            885              890              895
Pro Tyr Val Ile Val Pro Leu Lys Thr Gly Leu Gln Glu Val Glu Val
            900              905              910
Lys Ala Ala Val Tyr His His Phe Ile Ser Asp Gly Val Arg Lys Ser
            915              920              925
Leu Lys Val Val Pro Glu Gly Ile Arg Met Asn Lys Thr Val Ala Val
    930              935              940
Arg Thr Leu Asp Pro Glu Arg Leu Gly Arg Glu Gly Val Gln Lys Glu
945              950              955              960
Asp Ile Pro Pro Ala Asp Leu Ser Asp Gln Val Pro Asp Thr Glu Ser
            965              970              975
Glu Thr Arg Ile Leu Leu Gln Gly Thr Pro Val Ala Gln Met Thr Glu
            980              985              990
Asp Ala Val Asp Ala Glu Arg Leu Lys His Leu Ile Val Thr Pro Ser
            995             1000             1005
Gly Cys Gly Glu Gln Asn Met Ile Gly Met Thr Pro Thr Val Ile
    1010             1015             1020
Ala Val His Tyr Leu Asp Glu Thr Glu Gln Trp Glu Lys Phe Gly
    1025             1030             1035
Leu Glu Lys Arg Gln Gly Ala Leu Glu Leu Ile Lys Lys Gly Tyr
    1040             1045             1050
Thr Gln Gln Leu Ala Phe Arg Gln Pro Ser Ser Ala Phe Ala Ala
    1055             1060             1065
Phe Val Lys Arg Ala Pro Ser Thr Trp Leu Thr Ala Tyr Val Val
    1070             1075             1080
Lys Val Phe Ser Leu Ala Val Asn Leu Ile Ala Ile Asp Ser Gln
    1085             1090             1095
Val Leu Cys Gly Ala Val Lys Trp Leu Ile Leu Glu Lys Gln Lys
    1100             1105             1110
Pro Asp Gly Val Phe Gln Glu Asp Ala Pro Val Ile His Gln Glu
    1115             1120             1125
Met Ile Gly Gly Leu Arg Asn Asn Asn Glu Lys Asp Met Ala Leu
    1130             1135             1140
Thr Ala Phe Val Leu Ile Ser Leu Gln Glu Ala Lys Asp Ile Cys
    1145             1150             1155
Glu Glu Gln Val Asn Ser Leu Pro Gly Ser Ile Thr Lys Ala Gly
    1160             1165             1170
Asp Phe Leu Glu Ala Asn Tyr Met Asn Leu Gln Arg Ser Tyr Thr
    1175             1180             1185
Val Ala Ile Ala Gly Tyr Ala Leu Ala Gln Met Gly Arg Leu Lys
    1190             1195             1200
Gly Pro Leu Leu Asn Lys Phe Leu Thr Thr Ala Lys Asp Lys Asn
    1205             1210             1215
Arg Trp Glu Asp Pro Gly Lys Gln Leu Tyr Asn Val Glu Ala Thr
    1220             1225             1230
Ser Tyr Ala Leu Leu Ala Leu Leu Gln Leu Lys Asp Phe Asp Phe
    1235             1240             1245
Val Pro Pro Val Val Arg Trp Leu Asn Glu Gln Arg Tyr Tyr Gly
    1250             1255             1260
Gly Gly Tyr Gly Ser Thr Gln Ala Thr Phe Met Val Phe Gln Ala
    1265             1270             1275
```

```
Leu Ala Gln Tyr Gln Lys Asp Ala Pro Asp His Gln Glu Leu Asn
    1280                1285                1290
Leu Asp Val Ser Leu Gln Leu Pro Ser Arg Ser Ser Lys Ile Thr
    1295                1300                1305
His Arg Ile His Trp Glu Ser Ala Ser Leu Leu Arg Ser Glu Glu
    1310                1315                1320
Thr Lys Glu Asn Glu Gly Phe Thr Val Thr Ala Glu Gly Lys Gly
    1325                1330                1335
Gln Gly Thr Leu Ser Val Val Thr Met Tyr His Ala Lys Ala Lys
    1340                1345                1350
Asp Gln Leu Thr Cys Asn Lys Phe Asp Leu Lys Val Thr Ile Lys
    1355                1360                1365
Pro Ala Pro Glu Thr Glu Lys Arg Pro Gln Asp Ala Lys Asn Thr
    1370                1375                1380
Met Ile Leu Glu Ile Cys Thr Arg Tyr Arg Gly Asp Gln Asp Ala
    1385                1390                1395
Thr Met Ser Ile Leu Asp Ile Ser Met Met Thr Gly Phe Ala Pro
    1400                1405                1410
Asp Thr Asp Asp Leu Lys Gln Leu Ala Asn Gly Val Asp Arg Tyr
    1415                1420                1425
Ile Ser Lys Tyr Glu Leu Asp Lys Ala Phe Ser Asp Arg Asn Thr
    1430                1435                1440
Leu Ile Ile Tyr Leu Asp Lys Val Ser His Ser Glu Asp Asp Cys
    1445                1450                1455
Leu Ala Phe Lys Val His Gln Tyr Phe Asn Val Glu Leu Ile Gln
    1460                1465                1470
Pro Gly Ala Val Lys Val Tyr Ala Tyr Tyr Asn Leu Glu Glu Ser
    1475                1480                1485
Cys Thr Arg Phe Tyr His Pro Glu Lys Glu Asp Gly Lys Leu Asn
    1490                1495                1500
Lys Leu Cys Arg Asp Glu Leu Cys Arg Cys Ala Glu Glu Asn Cys
    1505                1510                1515
Phe Ile Gln Lys Ser Asp Asp Lys Val Thr Leu Glu Glu Arg Leu
    1520                1525                1530
Asp Lys Ala Cys Glu Pro Gly Val Asp Tyr Val Tyr Lys Thr Arg
    1535                1540                1545
Leu Val Lys Val Gln Leu Ser Asn Asp Phe Asp Glu Tyr Ile Met
    1550                1555                1560
Ala Ile Glu Gln Thr Ile Lys Ser Gly Ser Asp Glu Val Gln Val
    1565                1570                1575
Gly Gln Gln Arg Thr Phe Ile Ser Pro Ile Lys Cys Arg Glu Ala
    1580                1585                1590
Leu Lys Leu Glu Glu Lys Lys His Tyr Leu Met Trp Gly Leu Ser
    1595                1600                1605
Ser Asp Phe Trp Gly Glu Lys Pro Asn Leu Ser Tyr Ile Ile Gly
    1610                1615                1620
Lys Asp Thr Trp Val Glu His Trp Pro Glu Glu Asp Glu Cys Gln
    1625                1630                1635
Asp Glu Glu Asn Gln Lys Gln Cys Gln Asp Leu Gly Ala Phe Thr
    1640                1645                1650
Glu Ser Met Val Val Phe Gly Cys Pro Asn
    1655                1660

<210> SEQ ID NO 34
```

<211> LENGTH: 5091
<212> TYPE: DNA
<213> ORGANISM: Homo sapiens

<400> SEQUENCE: 34

```
ctgtccctct gaccctgcac tgtcccagca ccatgggacc cacctcaggt cccagcctgc      60
tgctcctgct actaacccac ctcccccotgg ctctggggag tcccatgtac tctatcatca     120
cccccaacat cttgcggctg gagagcgagg agaccatggt gctggaggcc cacgacgcgc     180
aaggggatgt tccagtcact gttactgtcc acgacttccc aggcaaaaaa ctagtgctgt     240
ccagtgagaa gactgtgctg acccctgcca ccaaccacat gggcaacgtc accttcacga     300
tcccagccaa cagggagttc aagtcagaaa aggggcgcaa caagttcgtg accgtgcagg     360
ccaccttcgg gacccaagtg gtggagaagg tggtgctggt cagcctgcag agcgggtacc     420
tcttcatcca gacagacaag accatctaca cccctggctc cacagttctc tatcggatct     480
tcaccgtcaa ccacaagctg ctaccgtgg gccggacggt catggtcaac attgagaacc      540
cggaaggcat cccggtcaag caggactcct tgtcttctca gaaccagctt ggcgtcttgc     600
ccttgtcttg ggacattccg gaactcgtca acatgggcca gtggaagatc cgagcctact     660
atgaaaactc accacagcag gtcttctcca ctgagtttga ggtgaaggag tacgtgctgc     720
ccagtttcga ggtcatagtg gagcctacag agaaattcta ctacatctat aacgagaagg     780
gcctggaggt caccatcacc gccaggttcc tctacgggaa gaaagtggag ggaactgcct     840
ttgtcatctt cggatccag gatggcgaac agaggatttc cctgcctgaa tccctcaagc     900
gcattccgat tgaggatggc tcgggggagg ttgtgctgag ccgaaaggta ctgctggacg     960
gggtgcagaa cccccgagca gaagacctgg tggggaagtc tttgtacgtg tctgccaccg    1020
tcatcttgca ctcaggcagt gacatggtgc aggcagagcg cagcgggatc cccatcgtga    1080
cctctcccta ccagatccac ttcaccaaga cacccaagta cttcaaacca ggaatgccct    1140
ttgacctcat ggtgttcgtg acgaaccctg atggctctcc agcctaccga gtccccgtgg    1200
cagtccaggg cgaggacact gtgcagtctc taacccaggg agatggcgtg ccaaaactca    1260
gcatcaacac acaccccagc cagaagccct tgagcatcac ggtgcgcacg aagaagcagg    1320
agctctcgga ggcagagcag gctaccagga ccatgcaggc tctgcctac agcaccgtgg     1380
gcaactccaa caattacctg catctctcag tgctacgtac agagctcaga cccggggaga    1440
ccctcaacgt caacttcctc ctgcgaatgg accgcgccca cgaggccaag atccgctact    1500
acacctacct gatcatgaac aagggcaggc tgttgaaggc gggacgccag gtgcgagagc    1560
ccggccagga cctggtggtg ctgccctgt ccatcaccac cgacttcatc ccttccttcc     1620
gcctggtggc gtactacacg ctgatcggtc cagcggccca gagggaggtg gtggccgact    1680
ccgtgtgggt ggacgtcaag gactcctgcg tgggctcgct ggtggtaaaa agcggccagt    1740
cagaagaccg gcagcctgta cctgggcagc agatgaccct gaagatagag ggtgaccacg    1800
gggcccgggt ggtactggtg gccgtggaca agggcgtgtt cgtgctgaat aagaagaaca    1860
aactgacaca gagtaagatc tgggacgtgg tggagaaggc agacatcggc tgcacccgg     1920
gcagtgggaa ggattacgcc ggtgtcttct ccgacgcagg gctgaccttc acgagcagca    1980
gtggccagca gaccgcccag agggcagaac ttcagtgccc gcagccagcc gcccgccgac    2040
gccgttccgt gcagctcacg gagaagcgaa tggacaaagt cggcaagtac cccaaggagc    2100
tgcgcaagtg ctgcgaggac ggcatgcggg agaaccccat gaggttctcg tgccagcgcc    2160
ggacccgttt catctcoctg ggcgaggcgt gcaagaaggt cttcctggac tgctgcaact    2220
```

| | |
|---|---|
| acatcacaga gctgcggcgg cagcacgcgc gggccagcca cctgggcctg gccaggagta | 2280 |
| acctggatga ggacatcatt gcagaagaga acatcgtttc ccgaagtgag ttcccagaga | 2340 |
| gctggctgtg gaacgttgag gacttgaaag agccaccgaa aaatggaatc tctacgaagc | 2400 |
| tcatgaatat attttgaaa gactccatca ccacgtggga gattctggct gtcagcatgt | 2460 |
| cggacaagaa agggatctgt gtggcagacc ccttcgaggt cacagtaatg caggacttct | 2520 |
| tcatcgacct gcggctaccc tactctgttg ttcgaaacga gcaggtggaa atccgagccg | 2580 |
| ttctctacaa ttaccggcag aaccaagagc tcaaggtgag ggtggaacta ctccacaatc | 2640 |
| cagccttctg cagcctggcc accaccaaga ggcgtcacca gcagaccgta accatccccc | 2700 |
| ccaagtcctc gttgtccgtt ccatatgtca tcgtgccgct aaagaccggc ctgcaggaag | 2760 |
| tggaagtcaa ggctgccgtc taccatcatt tcatcagtga cggtgtcagg aagtccctga | 2820 |
| aggtcgtgcc ggaaggaatc agaatgaaca aaactgtggc tgttcgcacc ctggatccag | 2880 |
| aacgcctggg ccgtgaagga gtgcagaaag aggacatccc acctgcagac ctcagtgacc | 2940 |
| aagtcccgga caccgagtct gagaccagaa ttctcctgca agggaccccca gtggcccaga | 3000 |
| tgacagagga tgccgtcgac gcggaacggc tgaagcacct cattgtgacc ccctcgggct | 3060 |
| gcggggaaca gaacatgatc ggcatgacgc ccacggtcat cgctgtgcat tacctggatg | 3120 |
| aaacggagca gtgggagaag ttcggcctag agaagcggca gggggccttg gagctcatca | 3180 |
| agaagggta cacccagcag ctggccttca gacaacccag ctctgccttt gcggccttcg | 3240 |
| tgaaacgggc acccagcacc tggctgaccg cctacgtggt caaggtcttc tctctggctg | 3300 |
| tcaacctcat cgccatcgac tcccaagtcc tctgcggggc tgttaaatgg ctgatcctgg | 3360 |
| agaagcagaa gcccgacggg gtcttccagg aggatgcgcc cgtgatacac caagaaatga | 3420 |
| ttggtggatt acgaacaac aacgagaaag acatggccct cacggccttt gttctcatct | 3480 |
| cgctgcagga ggctaaagat atttgcgagg agcaggtcaa cagcctgcca ggcagcatca | 3540 |
| ctaaagcagg agacttcctt gaagccaact acatgaacct acagagatcc tacactgtgg | 3600 |
| ccattgctgg ctatgctctg gcccagatgg gcaggctgaa ggggcctctt cttaacaaat | 3660 |
| ttctgaccac agccaaagat aagaaccgct gggaggaccc tggtaagcag ctctacaacg | 3720 |
| tggaggccac atcctatgcc ctcttggccc tactgcagct aaaagacttt gactttgtgc | 3780 |
| ctcccgtcgt gcgttggctc aatgaacaga gatactacgg tggtggctat ggctctaccc | 3840 |
| aggccacctt catggtgttc caagccttgg ctcaatacca aaaggacgcc cctgaccacc | 3900 |
| aggaactgaa cctgatgtg tccctccaac tgcccagccg cagctccaag atcacccacc | 3960 |
| gtatccactg ggaatctgcc agcctcctgc gatcagaaga gaccaaggaa aatgagggtt | 4020 |
| tcacagtcac agctgaagga aaaggccaag gcaccttgtc ggtggtgaca atgtaccatg | 4080 |
| ctaaggccaa agatcaactc acctgtaata aattcgacct caaggtcacc ataaaaccag | 4140 |
| caccggaaac agaaaagagg cctcaggatg ccaagaacac tatgatcctt gagatctgta | 4200 |
| ccaggtaccg gggagaccag gatgccacta tgtctatatt ggacatatcc atgatgactg | 4260 |
| gctttgctcc agacacagat gacctgaagc agctggccaa tggtgttgac agatacatct | 4320 |
| ccaagtatga gctggacaaa gccttctccg ataggaacac cctcatcatc tacctggaca | 4380 |
| aggtctcaca ctctgaggat gactgtcag cttcaaagt tcaccaatac tttaatgtag | 4440 |
| agcttatcca gcctggagca gtcaaggtct acgcctatta caacctggag gaaagctgta | 4500 |
| cccggttcta ccatccggaa aaggaggatg gaaagctgaa caagctctgc cgtgatgaac | 4560 |
| tgtgccgctg tgctgaggag aattgcttca tacaaaagtc ggatgacaag gtcaccctgg | 4620 |

```
aagaacggct ggacaaggcc tgtgagccag gagtggacta tgtgtacaag acccgactgg    4680
tcaaggttca gctgtccaat gactttgacg agtacatcat ggccattgag cagaccatca    4740
agtcaggctc ggatgaggtg caggttggac agcagcgcac gttcatcagc cccatcaagt    4800
gcagagaagc cctgaagctg gaggagaaga acactacct catgtggggt ctctcctccg     4860
atttctgggg agagaagccc aacctcagct acatcatcgg gaaggacact tgggtggagc    4920
actggcccga ggaggacgaa tgccaagacg aagagaacca gaaacaatgc caggacctcg    4980
gcgccttcac cgagagcatg gttgtctttg ggtgccccaa ctgaccacac ccccattccc    5040
ccactccaga taaagcttca gttataaaaa aaaaaaaaa aaaaaaaaaa a              5091
```

<210> SEQ ID NO 35
<211> LENGTH: 291
<212> TYPE: PRT
<213> ORGANISM: Plasmodium berghei

<400> SEQUENCE: 35

```
Ile Gln Ala Gln Arg Asn Leu Asn Glu Leu Cys Tyr Asn Glu Gly Asn
1               5                   10                  15

Asp Asn Lys Leu Tyr His Val Leu Asn Ser Lys Asn Gly Lys Ile Tyr
            20                  25                  30

Asn Arg Asn Thr Val Asn Arg Leu Leu Pro Met Leu Arg Arg Lys Lys
        35                  40                  45

Asn Glu Lys Lys Asn Glu Lys Ile Glu Arg Asn Asn Lys Leu Lys Gln
    50                  55                  60

Pro Pro Pro Pro Asn Pro Asn Asp Pro Pro Pro Asn Pro Asn
65                  70                  75                  80

Asp Pro Pro Pro Asn Pro Asn Asp Pro Pro Pro Asn Pro Asn
            85                  90                  95

Asp Pro Pro Pro Asn Ala Asn Asp Pro Pro Pro Asn Ala Asn
        100                 105                 110

Asp Pro Ala Pro Pro Asn Ala Asn Asp Pro Ala Pro Pro Asn Ala Asn
        115                 120                 125

Asp Pro Ala Pro Pro Asn Ala Asn Asp Pro Ala Pro Pro Asn Ala Asn
    130                 135                 140

Asp Pro Ala Pro Pro Asn Ala Asn Asp Pro Ala Pro Pro Asn Ala Asn
145                 150                 155                 160

Asp Pro Pro Pro Asn Pro Asn Asp Pro Ala Pro Pro Gln Gly Asn
            165                 170                 175

Asn Asn Pro Gln Pro Gln Pro Arg Pro Gln Pro Gln Pro Gln Pro Gln
        180                 185                 190

Pro Gln Pro Gln Pro Gln Pro Gln Pro Arg Pro Gln Pro Gln
    195                 200                 205

Pro Gln Pro Gly Gly Asn Asn Asn Asn Lys Asn Asn Asn Asn Asp Asp
    210                 215                 220

Ser Tyr Ile Pro Ser Ala Glu Lys Ile Leu Glu Phe Val Lys Gln Ile
225                 230                 235                 240

Arg Asp Ser Ile Thr Glu Glu Trp Ser Gln Cys Asn Val Thr Cys Gly
                245                 250                 255

Ser Gly Ile Arg Val Arg Lys Arg Lys Gly Ser Asn Lys Lys Ala Glu
            260                 265                 270

Asp Leu Thr Leu Glu Asp Ile Asp Thr Glu Ile Cys Lys Met Asp Lys
        275                 280                 285

Cys Ser Ser
    290
```

<210> SEQ ID NO 36
<211> LENGTH: 993
<212> TYPE: DNA
<213> ORGANISM: Plasmodium berghei

<400> SEQUENCE: 36

```
atggatgcaa tgaagagagg gctctgctgt gtgctgctgc tgtgtggagc agtcttcgtt      60
tcggctagcg gatccgatgg acaaaataaa agcatccaag cccaaaggaa cttaaacgag     120
ctatgttaca atgaaggaaa tgataataaa ttgtatcacg tgcttaactc taagaatgga     180
aaaatataca atcgaaatac agtcaacaga ttacttgccg atgctcccga aggaaaaaaa     240
aatgagaaaa aaaacgaaaa aatagagcgt aataataaat tgaaacaacc accaccacca     300
ccaaacccaa atgacccacc accaccaaac ccaaatgacc caccaccacc aaacccaaat     360
gacccaccac caccaaaccc aaatgaccca gcaccaccaa acgcaaatga cccagcacca     420
ccaaacgcaa atgacccagc accaccaaac gcaaatgacc cagcaccacc aaacgcaaat     480
gacccagcac caccaaacgc aaatgaccca gcaccaccaa acgcaaatga cccagcacca     540
ccaaacgcaa atgacccagc accaccaaac gcaaatgacc cagcaccacc aaacgcaaat     600
gacccaccac caccaaaccc aaatgaccca gcaccaccac aaggaaataa caatccacaa     660
ccacagccac ggccgcagcc acaaccacag ccacagccac aaccacagcc acagccacaa     720
ccacagccac gaccacagcc acaaccacag ccaggtggta ataacaataa caaaaataat     780
aataatgacg attcttatat cccaagcgcg gaaaaaatac tagaatttgt taaacagatc     840
agggatagta tcacagagga atggtctcaa tgtaacgtaa catgtggttc tggtataaga     900
gttagaaaac gaaaaggttc aaataagaaa gcagaagatt tgaccttaga agatattgat     960
actgaaattt gtaaaatgga taaatgttca agt                                 993
```